(12) United States Patent
Kammer et al.

(10) Patent No.: US 8,138,454 B2
(45) Date of Patent: *Mar. 20, 2012

(54) LIQUID WARMING DEVICE WITH BASIN DETECTION

(75) Inventors: Patrick Kammer, Greensboro, NC (US); Kevin Joseph Rackers, Summerfield, NC (US)

(73) Assignee: C Change Surgical LLC, Winston-Salem, NC (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/234,044

(22) Filed: Sep. 19, 2008

(65) Prior Publication Data

US 2009/0014547 A1 Jan. 15, 2009

Related U.S. Application Data

(60) Division of application No. 11/529,770, filed on Sep. 27, 2006, now Pat. No. 7,441,714, which is a continuation of application No. 11/209,283, filed on Aug. 23, 2005, now Pat. No. 7,128,275, and a continuation-in-part of application No. 29/226,136, filed on Mar. 24, 2005, now Pat. No. Des. 547,444.

(60) Provisional application No. 60/603,956, filed on Aug. 24, 2004, provisional application No. 60/603,957, filed on Aug. 24, 2004.

(51) Int. Cl.
*A61B 10/00* (2006.01)
*A61F 7/00* (2006.01)
*F27D 11/00* (2006.01)
*G05D 23/12* (2006.01)

(52) U.S. Cl. ........ 219/432; 219/430; 219/435; 219/491; 219/496; 219/518; 236/1 C; 604/114; 604/291

(58) Field of Classification Search .................. None
See application file for complete search history.

(56) References Cited

U.S. PATENT DOCUMENTS

| | | | | |
|---|---|---|---|---|
| 2,892,066 A | * | 6/1959 | Springer | 219/435 |
| 2,898,439 A | * | 8/1959 | Wantz et al. | 219/447.1 |
| 3,134,007 A | * | 5/1964 | Niblo | 219/447.1 |
| 3,892,945 A | * | 7/1975 | Lerner | 219/437 |
| 4,164,644 A | * | 8/1979 | Remsnyder et al. | 219/433 |
| 4,967,061 A | * | 10/1990 | Weber et al. | 219/438 |
| 5,129,033 A | * | 7/1992 | Ferrara et al. | 392/447 |
| 5,294,779 A | * | 3/1994 | Miquelot | 219/447.1 |
| 6,091,058 A | * | 7/2000 | Faries et al. | 219/430 |
| 6,268,591 B1 | * | 7/2001 | Thevenin | 219/414 |
| 6,274,847 B1 | * | 8/2001 | Hlava et al. | 219/433 |
| 6,768,085 B2 | * | 7/2004 | Faries et al. | 219/494 |
| 6,884,970 B2 | | 4/2005 | Lehman | 219/432 |

(Continued)

OTHER PUBLICATIONS

Office Action from related U.S. Appl. No. 11/529,770, 7 pgs (Feb. 26, 2007). Office Action from related U.S. Appl. No. 11/209,442, 6 pgs (Nov. 6, 2007).

(Continued)

*Primary Examiner* — Joseph M Pelham
(74) *Attorney, Agent, or Firm* — Andrew D. Sorensen; Shaoni L. Mitchell

(57) ABSTRACT

A liquid warming device for heating sterile fluids in a removable basin is described with emphasis on the properties of the basin interaction with the liquid warming device and with a drape that works with the basin to maintain a sterile field above the drape and the top of the basin. Also disclosed are various desirable aspects for a control system for a liquid warming device.

10 Claims, 17 Drawing Sheets

U.S. PATENT DOCUMENTS

| | | | |
|---|---|---|---|
| 7,128,275 B2 | 10/2006 | Kammer et al. | 236/1 |
| 7,279,660 B2 * | 10/2007 | Long et al. | 219/441 |
| 7,589,299 B2 * | 9/2009 | Fisher et al. | 219/445.1 |
| 7,745,759 B2 * | 6/2010 | Long et al. | 219/214 |
| 2002/0188259 A1 | 12/2002 | Hickle et al. | 604/189 |
| 2003/0000939 A1 * | 1/2003 | Faries et al. | 219/497 |
| 2008/0216668 A1 * | 9/2008 | Fraij et al. | 99/331 |

OTHER PUBLICATIONS

Office Action from related U.S. Appl. No. 11/529,770, 11 pgs (May 23, 2008).

Amendments to Claims from Response to Office Action Mailed May 23, 2008 from related U.S. Appl. No. 11/529,770, 8 pgs (Jun. 27, 2008).

* cited by examiner

Fig. 2
PRIOR ART
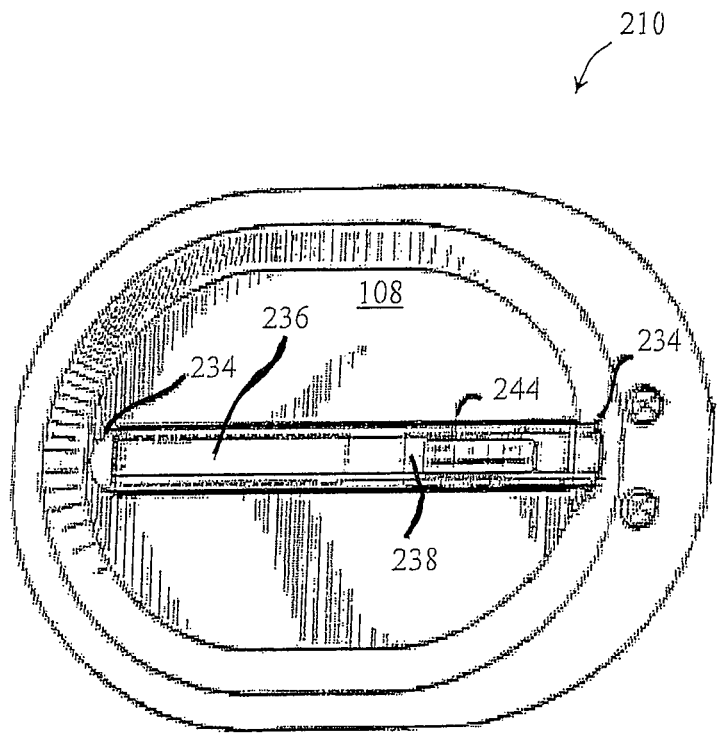
Fig. 2A
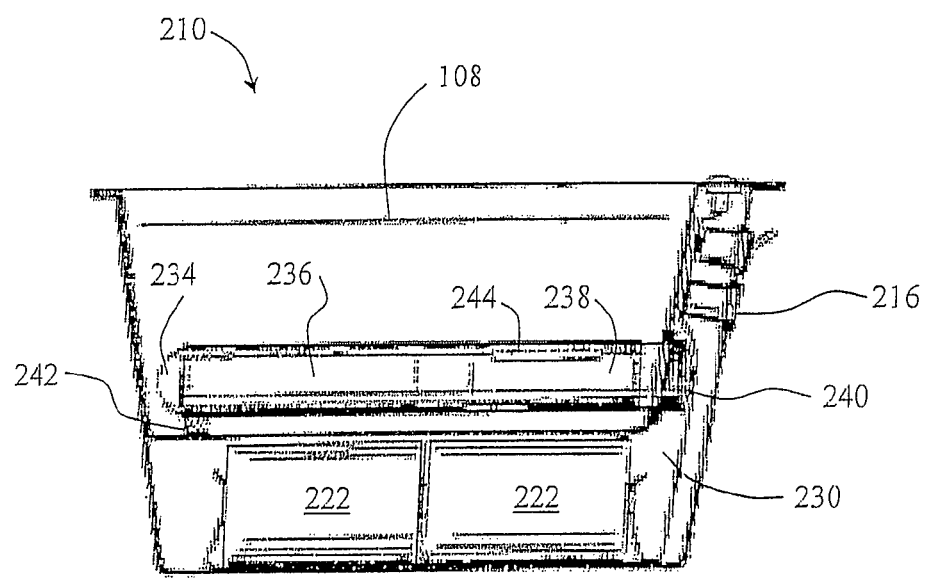
Fig. 2B (A)

(B)

(C)

(D)

LIQUID WARMING DEVICE WITH BASIN DETECTION

This application is a divisional of U.S. patent application Ser. No. 11/529,770 for Liquid Warming System filed Sep. 27, 2006. The '770 application claims priority to and incorporates by reference herein, a U.S. patent application Ser. No. 11/209,283 for Liquid Warming Device with Basin, now U.S. Pat. No. 7,128,275. The '275 patent claims priority to and incorporates by reference two provisional patent applications claimed in the '283 application: U.S. Provisional Patent Application 60/603,957 for Heating Element for Liquid Warming Device filed Aug. 24, 2004 and U.S. Provisional Patent Application 60/603,956 for Liquid Warming Device and Control System filed Aug. 24, 2004. The '275 patent claims priority to a then co-pending U.S. Design patent application 29/226,136 filed Mar. 24, 2005 for Hospital Basin with Channel, now U.S. Design Pat. No. D547,444 as the basin in the '444 patent is suitable for use with the present invention. This application claims priority to the three applications claimed for priority by the '275 patent and incorporates all three by reference.

Another application with common assignee is co-pending with the present application. The co-pending application is for a Heating Element for Liquid Warming Device with U.S. Ser. No. 11/209,430. The inventive aspects of heating elements disclosed in that application can be advantageously used with the present invention. The co-pending application is incorporated herein by reference in its entirety. Other related applications with common assignee are: Basin for Use in a Liquid Warming Device with U.S. Ser. No. 11/209,442; and Methods Using A Draped Liquid Warming Device with U.S. Ser. No. 12/168,590.

FIELD OF THE INVENTION

This invention relates to improvements in methods and apparatus for heating of sterile surgical liquids.

BACKGROUND OF THE INVENTION

Devices for the heating of sterile surgical liquids are known in the art. In a wide variety of surgical procedures, sterile fluids are used to irrigate the site of the surgery. It is important that the temperature of the fluids used be strictly controlled. As the portion of the brain that regulates body temperature is shut down with anesthesia, it is important that the introduction of sterile fluids does not cool the body core temperature. Clinical studies have indicated that a range of adverse consequences arise from a change in body core temperature as little as one to three degrees Celsius. The adverse consequences from mild perioperative hypothermia include hypertension and increased vascular resistance, cardiac events, coagulopathy, an increase risk of surgical wound infections, and delays in the body's ability to remove drugs from its systems. An additional potential adverse consequence is shivering which can increase metabolic rate up to 500% and thus increase demands for oxygen and the need to clear carbon dioxide. This list of complications is by no means exhaustive, but it highlights the critical importance in controlling the body core temperature. Careful control of the temperature of sterile irrigation fluids is an important part of controlling body core temperature.

The prior art includes various liquid warming devices to warm sterile fluid. Some are incorporated into a rolling cabinet for placement in a convenient place within the sterile field in an operating room so that sterile fluid is available at an appropriate temperature for uses in the surgery such as irrigation or lavage. It is recognized as desirable that the process for heating the fluid be capable of quickly heating the fluid to bring the fluid to the appropriate temperature. It is also recognized that having the heater apply so much heat that it damages the container used to hold the fluid is undesirable. Use of a heater that can expose personnel to heated surfaces that are hot enough to cause injury is undesirable and in some cases contrary to governmental regulations.

A conventional control system used in the art is shown in FIG. 1. A volume of sterile fluid 108 rests on a sterile drape 110 which in turn rests on an integrated basin 104 in the top of the liquid warming device. The sterile drape 110 thus shields the non-sterile liquid warming device from the sterile field. (One of skill in the art will recognize that the weight of the sterile fluid 108 would cause drape 110 to substantially conform to the shape of basin 104.) These drawings are intended to aid the disclosure of concepts, rather than serve as photographs, thus many gaps will exist in order to highlight the discrete elements.) The integrated basin 104, the drape 110 and the fluid 108 therein are heated by a heater 112 within the liquid warming device. The heater is controlled by measuring the temperature of the heater with a heater temperature detector 116. A heater controller 120 turns the heater on or provides additional current to cause the heater to heat up further if the measured temperature at the heater temperature detector is below a set point 124. As the temperature of the heater is regulated or controlled independently of the actual current temperature of the fluid in the drape, a participant in the surgery will test the temperature of the fluid by sticking a gloved finger 128 into the sterile fluid. This is somewhat effective as the target temperature for the sterile solution is often close to body temperature. If the fluid feels cool to the gloved finger, an instruction is given directly or indirectly to the controller 120 to increase the set point 124 for the heater. A subsequent gloved finger reaction is used to make additional corrections from time to time.

The temperature of the fluid 108 cannot be precisely predicted based on the set point of the last surgery as the temperature will be affected by the pouring of additional fluid into the drape as the fluid added may not be at the target temperature. The fluid temperature may also vary with changes in the positioning of the liquid warming device closer to airflow in the surgical suite, changes in humidity levels, or other factors. As the gloved finger test is rather subjective, it will give different results based on the person giving the test, the body temperature of the person, the length of time the gloved finger is inserted in the fluid, and other factors.

An additional problem in the prior art relates to maintaining the integrity of the sterile field. The integrity of the sterile field is essential to acceptable outcomes during surgery. Any breach that might indicate that the sterile field has become contaminated is taken very seriously. A breach that is undiscovered for a period of time is especially troublesome as it is difficult to assess when the breach was created and whether it caused the patient to be exposed to contaminants while vulnerable during surgery. Thus, it is no wonder that concerns from breaches in the sterile drapes 110 were taken very seriously. U.S. Pat. No. 6,910,485 for Medical Solution Thermal Treatment System and Method of Controlling System Operation in Accordance with Detection of Solution and Leaks in Surgical Drape Container addresses this concern. Likewise, issued U.S. Pat. No. 6,091,058 for Thermal Treatment System and Method for Maintaining Integrity and Ensuring Sterility of Surgical Drapes Used with Surgical Equipment teaches ways of reducing the risk of damage to surgical drapes from objects placed in the drape covered integrated basin.

Thus, problems associated with the recognized risk of a breach in a sterile drape have led others to develop various ways of reducing this risk or at least quickly detecting the breach.

In order to provide peace of mind to those working in the surgical theater, it would be advantageous to provide a way to use a standard disposable removable basin or a freestanding metal basin with a sufficiently high structural integrity that could be sterilized.

Plastic basins are ubiquitous in hospitals and are used in many ways. Plastic basins that are sterilized (for example through irradiation or ethylene oxide gas sterilization) can safely be used in the sterile field without a surgical drape placed over them. Metal basins are currently sterilized and safely reused just as a range of surgical implements are sterilized and reused.

The use of such basins would provide peace of mind as it is difficult to conceive of any activity in the sterile field that could cause a breach in a non-defective plastic or metal basin. A secondary benefit would be that standard gradation marks on the inside walls of the sterile removable basin would provide a visual indication of the amount of sterile fluid remaining in the sterile basin. As using basin gradation marks is done by hospital personnel in other contexts, the use of fluid gradation marks in this context will seem familiar.

One attempt to devise a device for heating fluid that used a substantial disposable basin is described in U.S. Pat. No. 5,129,033 for Disposable Thermostatically Controlled Electric Surgical-Medical Irrigation Bowl and Lavage Liquid Warming Bowl and Method of Use. FIGS. 2A and 2B illustrates the top and side views of the device taught in the '033 patent. A warming bowl 210 contains a heater assembly 234 which in turn contains heater 236, thermostat 238, and temperature indicator 244. The heater assembly 234 rests on support 242 and a passageway to an interior core 230 of the warming bowl 210 with the power supply 222.

The apparatus of FIG. 2 is different from FIG. 1 in that the device of FIG. 2 replaces the occasional measurements by gloved finger with continuous monitoring of the fluid temperature with a thermostat 238 placed in the heater assembly 234.

It appears that the intent of the '033 patent is for the entire assembly including the heater assembly 234, power supply 222, and various controls and indicator lights to be disposable as the '033 patent notes that "[i]rrigation liquid bowls are provided in pre-packaged pre-sterilized form ready for use, and they are non-reusable and disposable, in view of the stringent demands on aseptic conditions and also because of the high cost of reliable sterilization for reusable surgical instruments and accessories." Disposing of the electronics with the bowl would seem to make this solution prohibitively expensive.

But, it is hard to see a way to sterilize the '033 device as reuse from surgery to surgery would require a method of reliably sterilizing the heater assembly 234 along with the surface of the bowl that would come in contact with the sterile fluid 108. An additional complication is the need to use a sterilization process that does not impair the hermetic seal 240 as an impaired seal would provide a path for contamination of the inner core 230 and subsequent cross-contamination of the sterile fluid for a later surgery with blood products or other contaminants from an earlier surgery.

A second obvious problem with the solution proposed in the '033 patent is that the heater assembly 234 is simply in the way. Placing the heater assembly 234 in the area meant to contain the sterile fluid 108 solved problems for the design engineers but created lasting problems for the surgical staff who must work around the heater assembly 234 so as to avoid imparting a mechanical shock sufficient of causing the components to fail. The staff must also avoid contact with the heater assembly 234 sufficient to cause a breach in the casing of the heater assembly 234 or in the hermetic seal 240 which might allow fluid to contact non-sterilized areas or to adversely effect the electrical operation. Flooding the inner core 230 could be dangerous to surgical staff if the bowl 210 was using power provided through electrical plug receptacle 216 instead of running off batteries 222.

As noted above, even if the risk of causing a failure to the electrical components or seals is slight, such a risk diminishes the peace of mind of the surgical staff. Adding various detectors to quickly detect various failure modes might increase peace of mind somewhat but at yet another set of added costs to the single-use disposable unit.

The prior art lacks a solution for a fluid heating device using a removable basin that provides the benefits of using the actual temperature of the sterile fluid as an input to the control system without incurring the risks and problems inherent in the use of such a temperature probe.

SUMMARY OF THE DISCLOSURE

A liquid warming device with a cavity to receive a removable basin is disclosed. In a preferred embodiment the liquid warming device uses a basin drape with a hole in the drape to allow the bottom portion of the basin to extend down below the drape to interact with the liquid warming device while the drape and the top of the basin provide a sterile barrier between the top of the liquid warming device and the sterile field. The control system for the liquid warming device operates based on a temperature measurement indicative of the temperature of the liquid contained in the basin. In a preferred embodiment, this temperature is sensed by a temperature sensor located in a temperature well that protrudes into the liquid in the basin. In a preferred embodiment, the distal end of the temperature sensor engages with the temperature well in an interference fit so that there is good thermal contact between at least a portion of the distal end of the temperature sensor and the interior of the temperature well. In a preferred embodiment, a basin indicator such as a limit switch actuator and limit switch confirm the presence of a suitable basin before allowing energy to be applied so that energy is not applied unless there is an appropriate basin in the proper location in the cavity of the liquid warming device.

Additional details concerning the various preferred embodiments of the basin, drape, liquid warming device including the control system for the liquid warming device, and some alternative embodiments are disclosed through examples to illustrate the various aspects of the present invention.

BRIEF DESCRIPTION OF THE DRAWINGS

FIGS. 2A and 2B illustrate a prior art solution of a disposable device with a temperature sensor permanently suspended in the fluid to be measured.

DETAILED DESCRIPTION OF THE DISCLOSED EMBODIMENTS

The present invention will now be described more fully hereinafter with reference to the accompanying drawings, in order to disclose selected embodiments. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
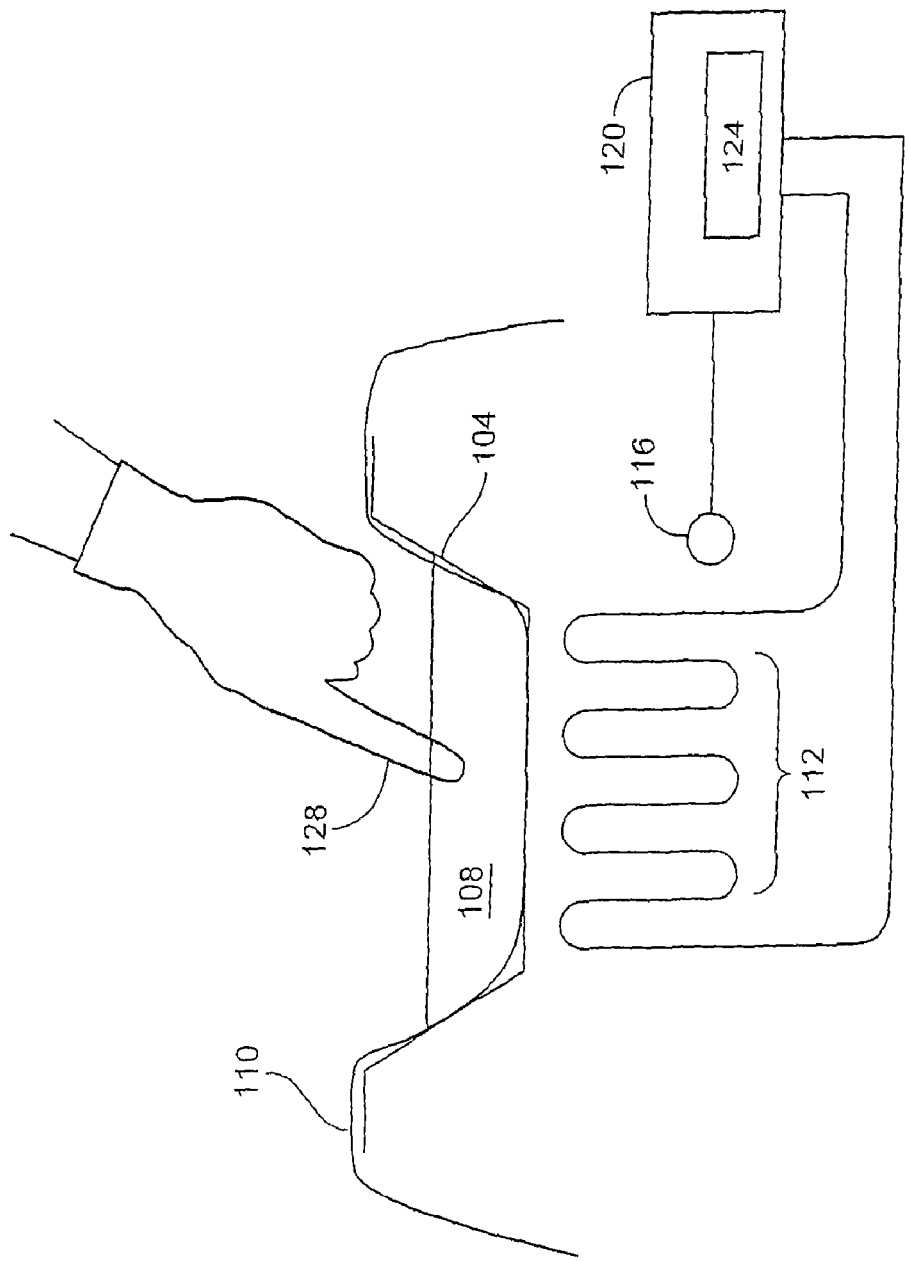
FIG. 1 illustrates a prior art method of controlling fluid temperature by using a gloved finger to sense the temperature and adjusting the heater set point accordingly.
Figure 3:
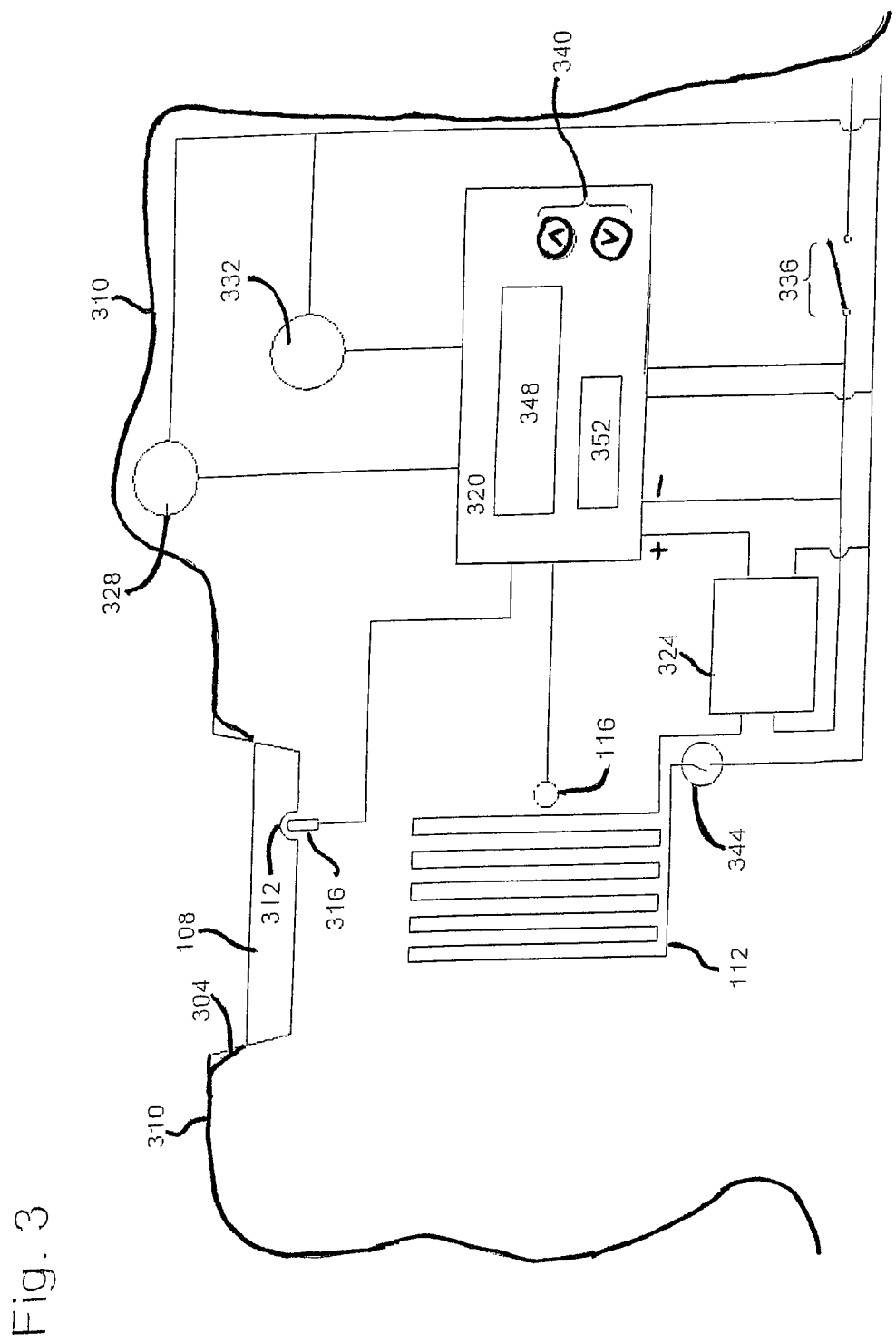
FIG. 3 illustrates one embodiment of the present invention including a dual-set point control scheme to control the temperature of fluid 108 in basin 304.

FIG. 3 illustrates a first embodiment of the present invention. The sterile fluid 108 is inside modified basin 304 with integral thermocouple well 312 and temperature sensor 316. The heater 112 selectively applies heat that is transferred to the basin 304 and the fluid 108. The fluid warming device has a main on/off switch 336. Some heating elements come with a mechanical thermostat 344 such as a bimetallic thermostat to provide a secondary protection against a failed control system. This second mechanical thermostat 344 acts as a switch to shut off the heater if the temperature exceeds a set temperature. This should be set to a temperature that is low enough that the mechanical thermostat opens before the heater can overheat an empty basin. For example a mechanical thermostat set for 220 degrees Fahrenheit might be acceptable for use with a basin capable of withstanding permanent exposure to a 300 degree Fahrenheit heat source.

In the preferred embodiment, a modified surgical drape 310 is connected to some combination of the upper rim of the basin 304 or its outside wall so that the basin 304 extends down through the hole in the surgical drape. As the modified surgical drape 310 does not run along the bottom of the basin, the drape 310 does not interfere with the interaction of the thermocouple well 312 and the control system. Nor does the drape 310 get between the bottom of the basin 304 and the heat coming from heater 112 to the bottom of the basin. The drape basin combination would typically be combined together as part of preparing a surgical kit and the drape would encircle the basin bottom with the remainder of the drape folded or pooled in the cavity of the basin so that the basin could be placed into the fluid warming device and once properly positioned, the drape could be unfolded from the basin to cover the top and upper sides of the fluid warming device to maintain a sterile field.

The interaction between the drape 310 and the basin 304 could be a simple interference fit such that the basin once inserted into a hole in the drape stretches the drape so that the drape stays attached to the basin sufficiently for it to maintain the sterile field. Alternatively, the drape could be bonded to the outer wall of the basin or to the underside of the rim of the basin.

FIG. 3 shows drape 310 extending downward to cover the components in FIG. 3. This is illustrative of the point that the drape is used to maintain the sterile field, but one of skill in the art will recognize that individual components shown in FIG. 3 are apt to be inside a housing and not in direct contact with the drape. One exception is the tops of the indicator lamps 328 and 332 (discussed below) which must remain visible through the drape as discussed in detail below. Also as discussed below some controls may be placed outside of the sterile field and thus located below where the drape ends on the liquid warming device.

The user can alter a target temperature 352 for the fluid through the use of input keys 340. The target temperature 352 and the current temperature of the fluid can be displayed on a display 348. The input keys 340 and the display 348 in the preferred embodiment are placed low on the housing so that these components are below the drape 310 and outside the sterile field. One of skill in the art will recognize that special window could be placed in the drape or the drape could be made of material with optical properties that allow a standard LED display to be read through the drape.

Thermocouple Well

One possible embodiment is to use a thermocouple well 312 made of a material that conducts heat, such as metal, but is preferably made so as to have low thermal mass in order to be very responsive to changes in the temperature of the sterile fluid. Using a small diameter well and thin gauge material is useful for obtaining a low thermal mass. The thermocouple well can be a hemispheric protrusion into the sterile fluid but could also be some other shape. Preferably the thermocouple well will present a three-dimensional surface of conductive material to the sterile fluid rather than a plate of conductive material at the top of a non-conductive protrusion.

In a preferred embodiment, the thermocouple well is made of the same material as the basin as this will serve to decrease the cost of fabrication and eliminate the potential for leakage at the border between two dissimilar materials. A thermocouple well incorporated into a polypropylene basin will afford significant responsiveness of the thermocouple in the well as the thermocouple/well combination will be extended out into the fluid.

Figure 4A:
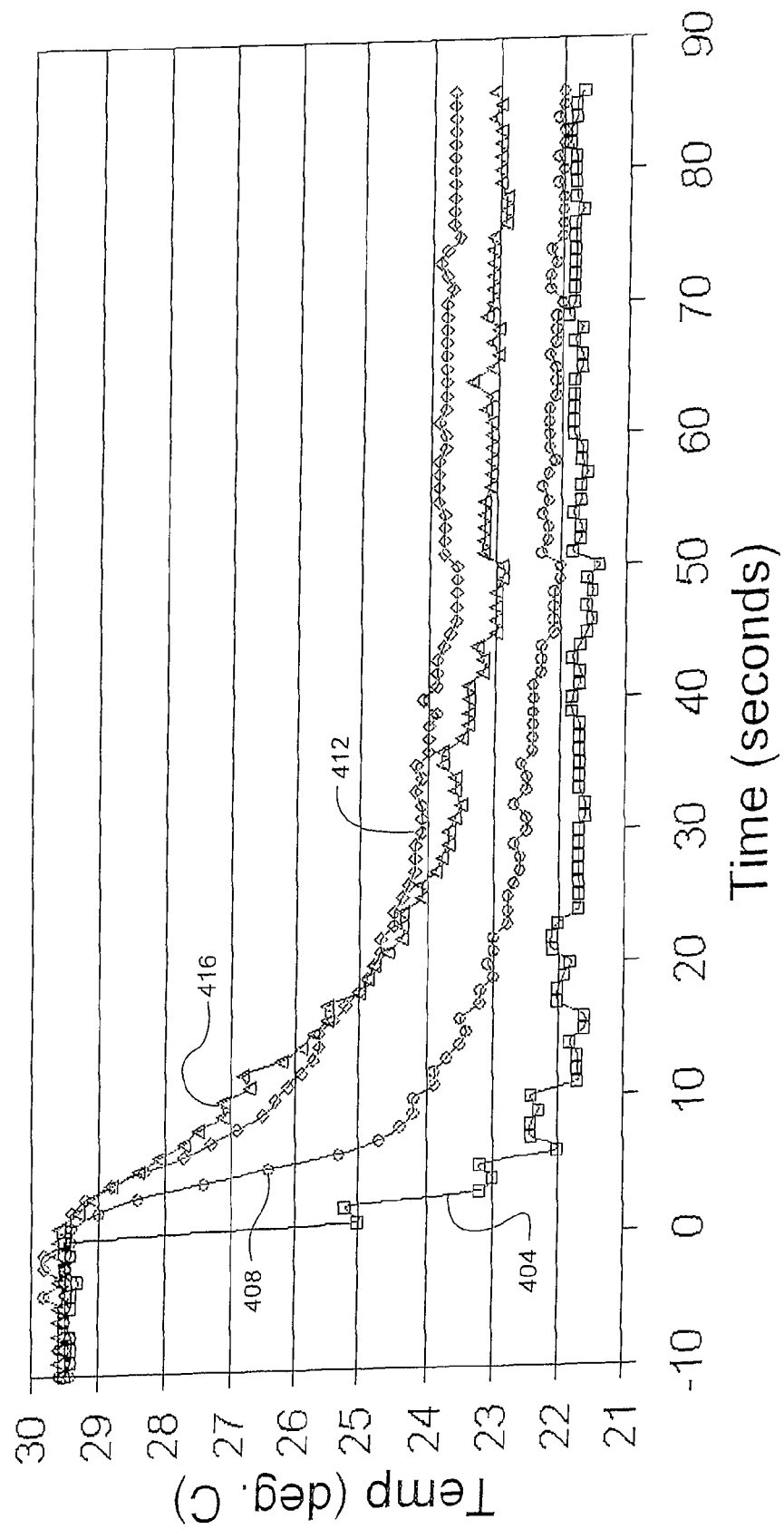
FIGS. 4A and 4B present experimental data showing how a temperature sensor in a thermocouple well reacts to changes in fluid temperature relative to temperature sensors placed in other locations.
Figure 4B:
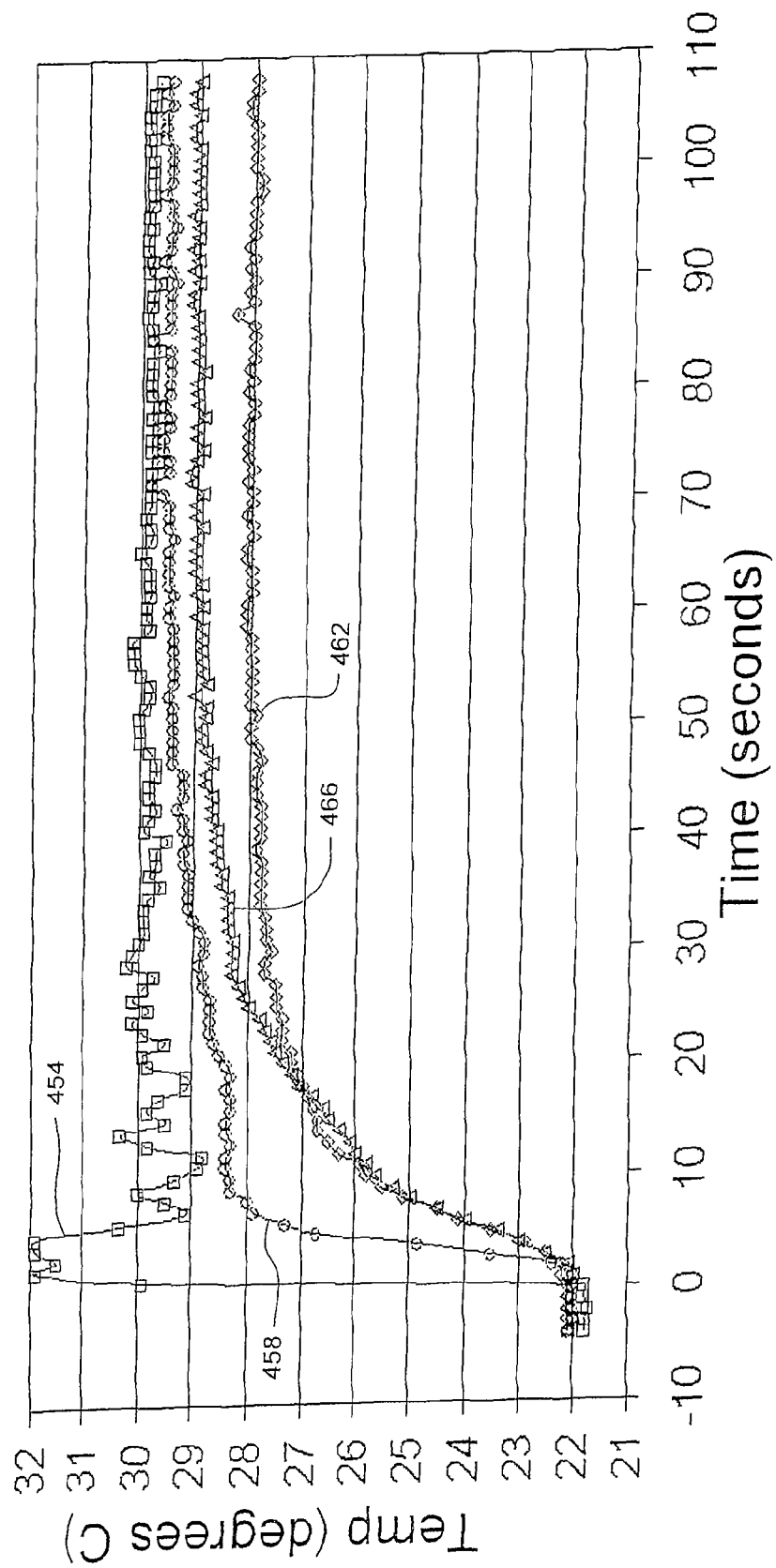

The efficacy of using a thermocouple well is illustrated in FIGS. 4A and 4B. FIGS. 4A and 4B show the responsiveness of a thermocouple placed in thermocouple well divot formed in the bottom of a six liter polypropylene basin. FIG. 4A shows the responses of four thermocouples to track the change in temperature in a basin as cold water is added. The test was done without a heater in order to focus on the ability of the thermocouples to track a change in temperature. A basin with two liters of water at 29.7 degrees Celsius had a liter of 5 degree Celsius water added (unusually cold water to make it easier to see the differences between the various measuring points). Curve 404 represents the data as measured by a thermocouple suspended in the water. Curve 404 is as expected, the most responsive to the change in temperature. Curve 408 is the curve of data as measured through a thermocouple in a thermocouple well extending into the fluid. This curve is significantly more responsive than the curves from data obtained from thermocouples placed in contact with the bottom of the basin (curve 412) or the side of the basin below the water line (curve 416). In less than a minute after the significant movement in temperature from the addition of frigid water, the temperature obtained from the thermocouple well is within a fraction of a degree Celsius of the temperature obtained from the thermocouple suspended in the fluid.

FIG. 4B shows the results when a basin with three liters of 22 degree Celsius water received an additional liter of 55 degree Celsius water. Again curve 454 for the data from the thermocouple suspended in the water is the most responsive to the change in temperature of the water. Again curve 458 for the data obtained from the thermocouple in the thermocouple well extending into the fluid is the second most responsive and quickly converges on curve 454. The curves 462 and 466 for data collected from thermocouples on the bottom and the side of the basin are again less responsive to the change in temperature. Error or bias in the thermocouples does not seem to explain the deviation of these curves from the new water temperature as the four curves were all substantially the same at the steady state before the introduction of the hot water.

Thus, using a thermocouple placed in a thermocouple well made of the same material as the basin (even relatively non-conductive material such as polypropylene) is a viable option to obtaining a responsive indication of fluid temperature without the significant problems associated with suspending a thermocouple in the fluid to be measured while trying to maintain a sterile field and not interfere with the work of the surgical staff.

A non-intuitive advantage of using such a thermocouple well rather than a thermocouple well made of a highly conductive material, such as a metal, is that the thermocouple well made of non-conductive material is less prone to being influenced by the temperature of the heat source below the basin. More specifically, there is an advantage to using the relatively non-conductive plastic material for the thermocouple well in that the elevated temperature of the heat source cannot travel easily through the relatively non-conductive plastic thermocouple well to convey heat to the tip of the thermocouple.

Dual Set Points

Returning to FIG. 3, a fluid temperature sensor 316 (such as a thermocouple) is placed in thermal contact with the thermocouple well 312 and in electrical contact with a fluid temperature controller 320. The fluid temperature controller 320 varies the set point for the temperature of the heater 112 which is measured by the heater temperature detector 116. As described in more detail below the set point for the heater is not the same as the target temperature 352 for the fluid.

In order to isolate the fluid temperature controller 320 from the current used in the heater 112, a solid state relay 324 is used to translate control signals from the fluid temperature controller 320 to effectively close a switch and provide current to the heater 116.

Visual Indicators

In a preferred embodiment, two visual indicators are provided that can be seen from a distance to allow those participating in the surgery to check the fluid temperature status from afar. When the At-Temperature indicator lamp 328 is lit, this conveys that the fluid temperature is at the target temperature or within a certain tolerance of that target temperature. In contrast, when the Out-of-Range indicator lamp 332 is lit, it indicates that the liquid warming device has power and the main on/off switch 336 is turned on but the fluid is not within a certain tolerance of the target temperature. In a preferred embodiment this light is not lit unless the limit switch (discussed below) indicates that a basin is present.

In the preferred embodiment, a single Out-of-Range indicator is sufficient as the staff would typically know whether they had added cool water or hot water to the basin. In the event that the staff was not sure whether the temperature was above or below the desired range, the specific temperature could be obtained from the display 348. This gives the staff the information necessary to make an informed quantitative decision to use out-of-range fluid if the particular intended use of the out-of-range fluid would be acceptable. As noted below, one of skill in the art can appreciate that the Out-of-Range indicator could be revised to be an above range indicator and a below range indicator.

A preferred embodiment uses a green lamp for At-Temperature and either a red lamp or most preferred, a yellow lamp for Out-of-Range. As the preferred embodiment separates the liquid warming device from the sterile field through the use of the surgical drape 310, the indicator lights selected (size, brightness, degree of protrusion from the surface) must be suitable for providing an adequate visual signal even through the drape material which for some drapes is not fully transparent. LED lights can be suitable for at least some drape materials. Ideally the light source should be of the type that projects light towards the drape as this helps make the visual indicator visible. While not preferred, the lights could be made more visible by placing a window of substantially transparent material in the drape so that when appropriately placed on the fluid warming device the window is placed over the visual indicator lights.

The portion of the indicator light assembly that comes in contact with the surgical drape must operate at a temperature that can be maintained in contact with a surgical drape for an extended period of time without damaging the surgical drape. An extended period of time would mean 24 hours of contact without damaging the drape.

One could provide further detail by using separate indicator lamps for above the temperature target range and one for below the temperature target range. Perhaps, blue for too cold and red for too hot. Likewise, one could add additional indicator lamps to distinguish between close to the target temperature range but still out of range from an indication that the current fluid temperature is further from the target temperature range. For instance once could use a yellow lamp for close but not quite in range. One of skill in the art will note that flashing lights could be used to convey something different from constant lights. For example a flashing the In-Range and Out-of-Range lights might convey that the temperature is almost in-range.

Another alternative for indicator lights is to provide one light to indicate that the warming device is turned on and a second light to indicate that power is currently being applied to the heater 112. When the fluid temperature is significantly below the target temperature, the heater-on light will be lit for an extended period of time. As the temperature of the sterile fluid approaches the target temperature, the heater will be turned on and off thus causing the heater-on light to turn on and off. Contingent on the control scheme implemented to control the heater, the steady state operation of the control system to maintain the temperature of the sterile fluid 108 may be frequent switching of the heater on and off.

Optionally, the temperature of the sterile fluid can be printed along with the time or alternatively this information can be stored for printing later. In either case, a history of the temperature over time can be used in connection with other surgical records to document that the sterile fluid was at an appropriate temperature when used.

Temperature Detector Choices

The preferred embodiment uses a grounded thermocouple for the fluid temperature sensor 316 as a grounded thermocouple gives a fast response to changes in temperature. Ideally, the thermocouple should have a low thermal mass in keeping with the goal to have the system be responsive to changes in fluid temperatures. The preferred embodiment uses a RTD for heater temperature detector 116 rather than a second grounded thermocouple as that would lead to a ground loop. Secondarily, a RTD is less vulnerable to interference from the electro-magnetic field from the heater. Note, the use of the term "thermocouple well" is meant to convey a common name for such a protrusion and is not meant to imply that the temperature sensor must be a thermocouple.

Fluid Temperature Controller

Figure 5:
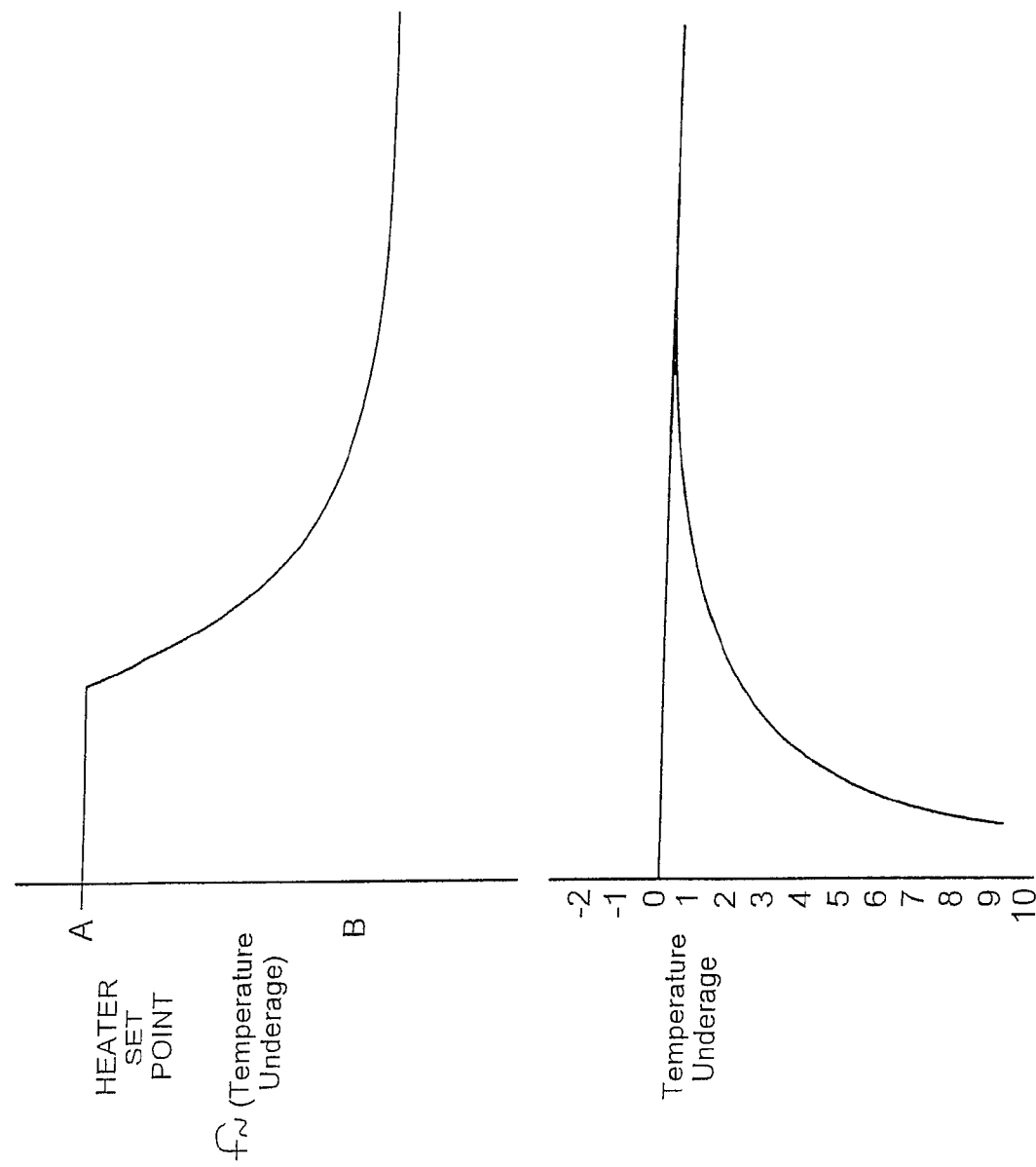
FIG. 5 shows the use of a dual-set point system to change the set point for a heater temperature based on the proximity of a measured fluid temperature to a target temperature for the fluid.

The preferred embodiment uses a cascade control scheme as illustrated in FIG. 5. The system responds to the current temperature underage. The temperature underage is the difference between the target temperature and the current temperature of the sterile fluid. If the target temperature is set to 100 degrees Fahrenheit then a current fluid temperature of 90 degrees Fahrenheit would indicate a 10 degree temperature underage. In the preferred embodiment, the target temperature can be modified by input keys 340.

The fluid temperature controller is set to operate the heater at a maximum temperature shown on FIG. 5 as temperature A. The preferred embodiment chooses a relatively high temperature in order to quickly reduce the temperature underage, but at the same time chooses a temperature that is well below the temperature that would damage the removable basin. For example when using a removable basin made of polypropylene, a suitable conservative maximum temperature might be 180 degrees Fahrenheit. The removable basin can be made of any range of suitable material such as stainless steel. The choice of basin material may impact the choice of maximum temperature. At some point the tolerance to heat of the material used in the removable basin may be so high as to become irrelevant that the maximum temperature is selected based on other factors such as safety of the personnel.

The steady state temperature shown as B on FIG. 5 is not a programmed number but is the temperature of the heater that maintains the sterile fluid at the desired target temperature. The temperature needed to maintain the fluid at 100 degrees Fahrenheit will be slightly higher in an operating suite with a lower ambient air temperature than in a similarly situated operating suite with a higher ambient air temperature. In the preferred embodiment, the maximum temperature is used as the set point for the heater until the temperature of the sterile fluid is relatively close to the target temperature. For example, the maximum temperature can be used until the temperature underage is only 2 degrees Fahrenheit.

As the temperature of the sterile fluid approaches the target temperature, the set point for the heater is reduced thus slowing the rate of temperature increase of the sterile fluid. A suitable means for controlling the heater set point is the use of a standard PID (Proportional Integral Derivative) controller. An example of a suitable PID controller is a Series 988 Controller manufactured by Watlow of Winona, Minn., www.watlow.com/products/controllers.

As the controller seeks to reduce the output of the heater, the controller operates the relay to reduce the percentage of time that the heater receives power. Thus, a heater maintaining fluids at the desired fluid temperature would be provided with power a smaller percentage of the time compared with the same heater bringing the same volume of fluid to the desired temperature as the latter is operating at a higher set point temperature and the below temperature volume of fluid absorbs heat more readily.

A less preferred embodiment would remove the ability of the user to adjust the target temperature and would essentially have a fixed target temperature. In such a case, the heater set point would become a function of the sterile fluid temperature as there would be a consistent relationship between sterile fluid temperature and the temperature underage.

Based on the data sets discussed in connection with FIG. 4A and FIG. 4B, the use of a basin with the temperature sensor placed below the basin or outside a wall of the basin would tend to be less responsive to the changes in fluid temperature than a temperature sensor placed in thermocouple well. When setting a controller for such a system, it may be necessary to stop operating the heater at the fixed elevated set point (see A on FIG. 5) at a larger underage value so that the combination of the lagging response of a temperature sensor placed below the basin and the elevated heater set point do not drive the temperature of the heated sterile fluid above the desired target temperature. Conversely, the use of a thermocouple well for the temperature sensor to provide a more representative temperature to the controller allows the use of the elevated heater temperature longer and thus shortens the time needed to bring a cooled basin of fluid to the target temperatures.

Limit Switch

Figure 6:
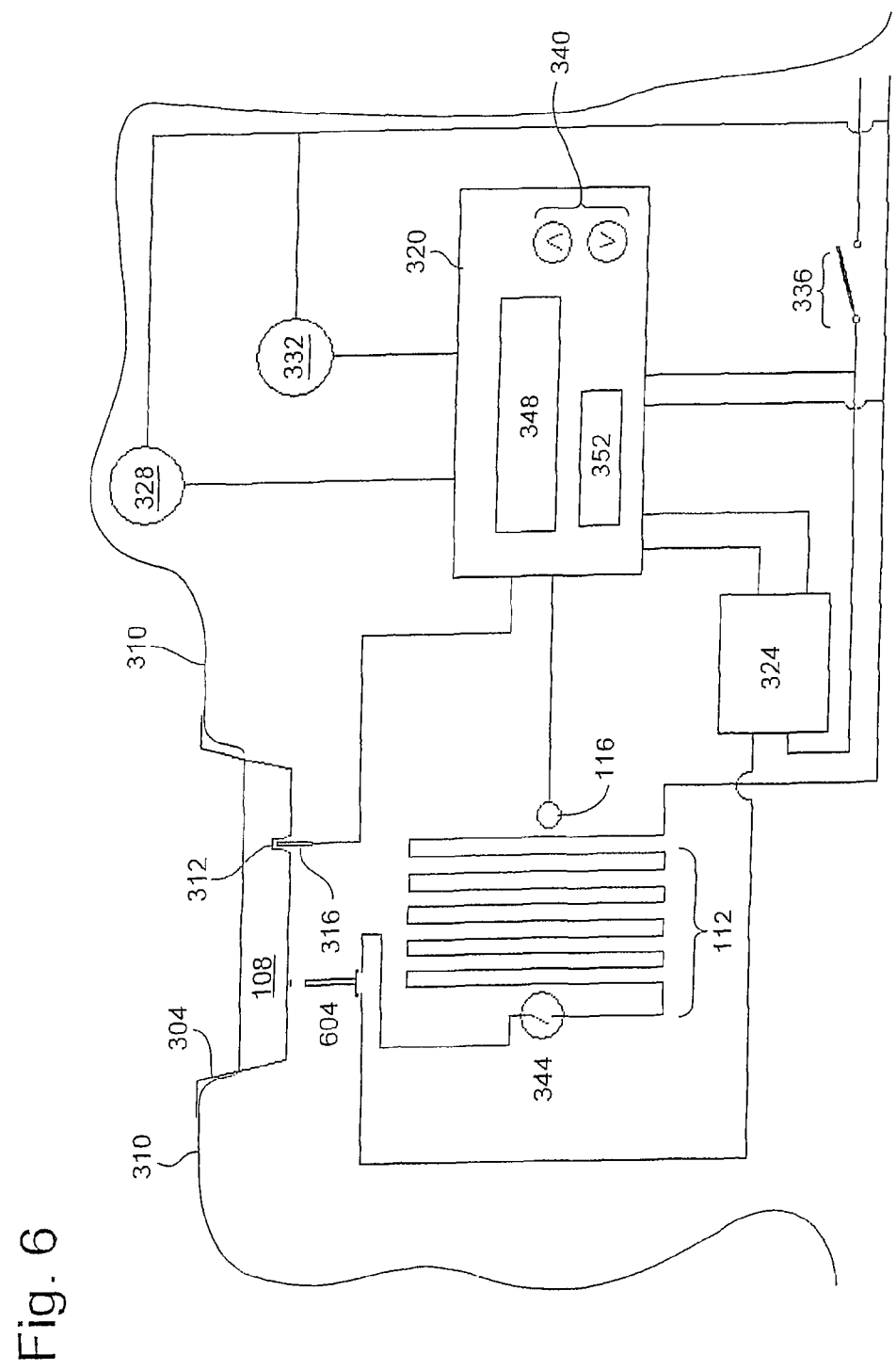
FIG. 6 shows another embodiment of the present invention that modified the embodiment in FIG. 3 to add a limit switch 604.
Figure 7:
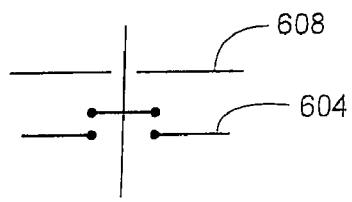
FIGS. 7A, 7B, 7C and 7D provide a more detailed explanation of the interaction of the limit switch 604 with various basins.
Figure 7:
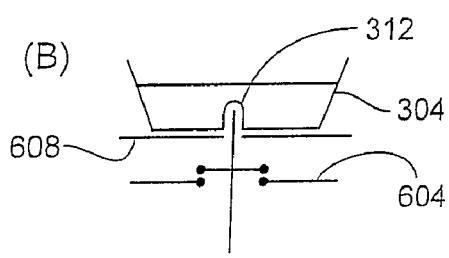
Figure 7:
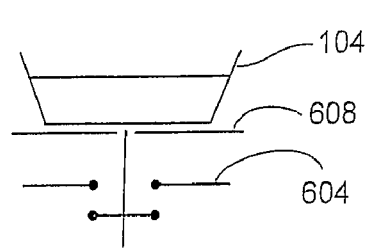
Figure 7:
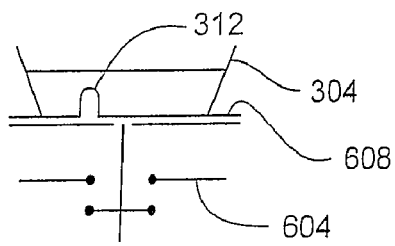

A modification of FIG. 3 is shown in FIGS. 6 and 7. A basin limit switch 604 is added to prevent power from reaching the heater 112 unless it is appropriate to allow the heater to get hot. In the most preferred embodiment the basin limit switch 604 detects two conditions. The first condition is the absence of a removable basin. The second condition is the use of a basin without a corresponding well as this basin may not be able to tolerate the application of heat at maximum temperature A as temperature A is chosen based on a specific basin material. A careful observer will note that while FIG. 6 depicts limit switch 604 as a limit switch and as a reminder places the limit switch near the basin 304, it does not show the interaction between the limit switch and the temperature sensor or the thermocouple well. As this is primarily a control system drawing, FIG. 6 does not show the mechanical interaction between the limit switch 604 and the temperature sensor's insertion in the thermocouple well 312 as this is better conveyed by other drawings and text.

FIG. 7 illustrates the various cases. In FIG. 7A, the thermocouple protrudes up through the heater plate surface 608 but does not contact anything at all. This causes the limit switch activated by the amount of extension of the thermocouple to ride high and fail to close the basin limit switch 604.

FIG. 7B illustrates the thermocouple rising through the heater plate surface 608 and contacting the top of a thermocouple well 312 in a basin 304. In FIG. 7B the limit switch 604 is closed and current can pass to the heater to heat the sterile fluid.

FIG. 7C illustrates a basin 104 without a corresponding thermocouple well in the appropriate location. The bottom of the basin 104 pushes the thermocouple down to the extent that the limit switch is opened and no current is provided to the heater. This prevents the heater from applying a maximum temperature that is beyond what the unknown basin can withstand. The operation of the limit switch 604 as shown in FIG. 7A or 7C could prevent the application of heat to supplies placed in the fluid heating device that are not intended to be heated. While it is not suggested that the fluid heating device be used to carry supplies in this way, a limit switch with an over-travel position that is open is less likely to inadvertently allow heat to be applied to something other than a basin with an appropriate thermocouple well.

FIG. 7D is another case of the thermocouple being depressed too far and thus opening the basin limit switch. In FIG. 7(d) the thermocouple well 312 is not properly aligned with the thermocouple. Continuing to operate with the basin in a misaligned position is apt to be sub-optimal as the thermocouple will not receive the current fluid temperature and may be partially isolated from the actual temperature. Optionally, the warming basin controls provide an indication (such as another indicator lamp) whenever the removable basin is pushing the limit switch open (over-travel) so that an operator can detect and correct the problem.

One of skill in the art will recognize that the illustrations in FIG. 7 convey the concepts and situations addressed by the limit switch and are not necessarily representative of the specific arrangement of the limit switch itself. For example, the limit switch could be implemented with a spring loaded horizontal component that moves in and out as a vertical piece of varying width moves up and down.

Figure 8A:
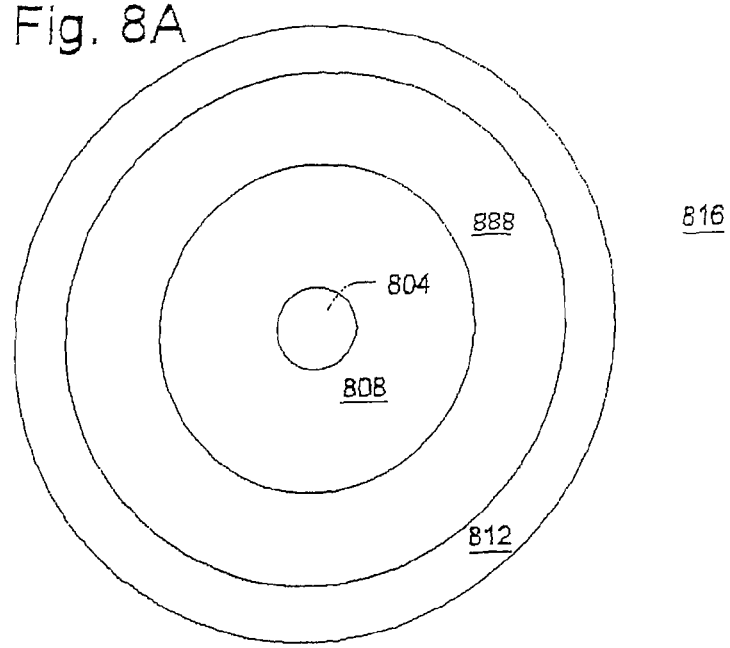
FIGS. 8A, 8B and 8C provide details of a preferred embodiment where the basin 850 with integrated thermocouple well 854 pushes down on the limit switch actuator 808 when the temperature sensor 804 is inserted into the thermocouple well 854 by placement of the basin 850.

An alternative embodiment of the limit switch of FIG. 7 is illustrated in FIG. 8. FIG. 8A is a view from the top of the temperature sensor 804 surrounded by limit switch actuator 808, limit switch guide 888, insulating zone 812, and conductive material 816. The conductive material conveys heat from the heater below the conductive material to the bottom of the basin.

In this embodiment the temperature sensor 804 is substantially isolated from the temperature of the conductive material 816 by the limit switch guide 888 and the insulating zone 812. In a preferred embodiment the limit switch actuator 808 also serves as a thermal insulator to help isolate the temperature sensor 804 from the conducting material 816. Placement of limit switch actuator 808 surrounding the temperature sensor 804 helps protect the temperature sensor 804 when the basin is not in the cavity of the liquid warming device and staff may be tempted to place items in the cavity. While the limit switch actuator and limit switch could be placed away from the temperature sensor, it is preferable to have the limit switch actuator near the temperature sensor as this minimized the number of places that have components that stick through the layer containing the resistive heater. By minimizing the number of places where the resistive heater is not present, the design provides for more rapid and uniform heating of the liquid through the basin.

Figure 8B:
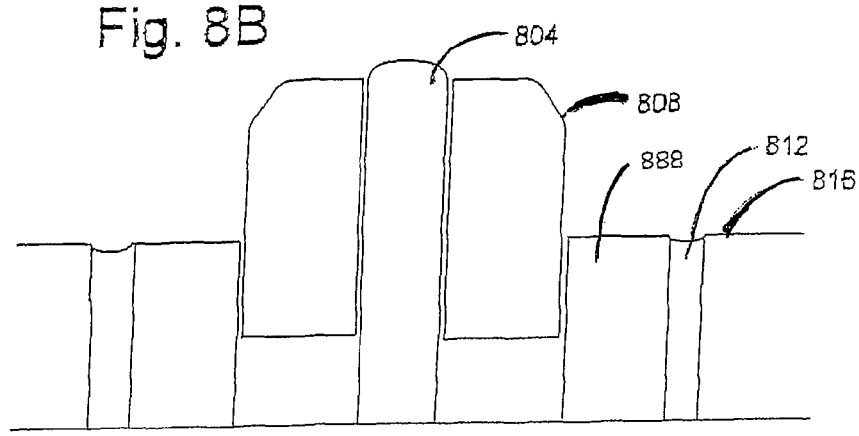

FIG. 8B is a side view of the components shown in FIG. 8A. From the side, one can see the temperature sensor 804 protruding from the extended limit switch actuator 808. FIG. 8B also shows the relative position of the limit switch guide 888, the insulating zone 812 and the start of the conductive material 816.

Figure 8C:
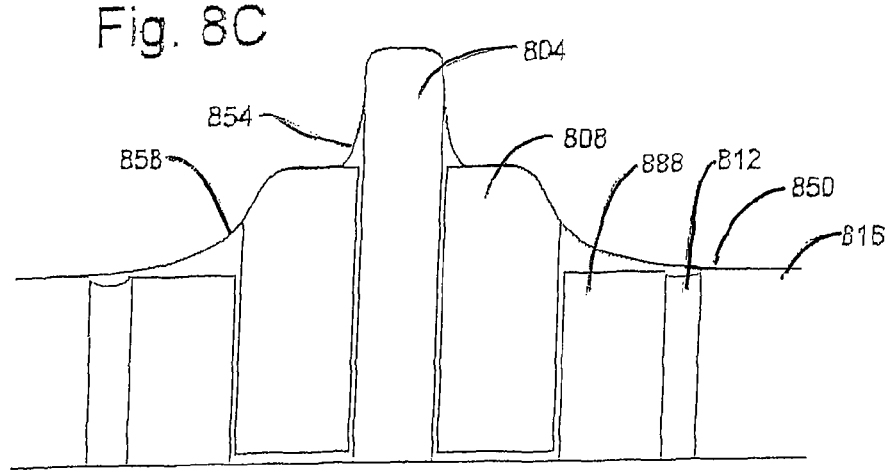

FIG. 8C shows a partial cut-away view of a basin 850 with integrated thermocouple well 854. When the basin 850 is placed to align the thermocouple well 854 above the temperature sensor 804, the basin 850 pushes down on the limit switch actuator 808 which moves downward relative to the temperature sensor 804, limit switch guide 888, insulating zone 812, and conductive material 816. Movement of the limit switch actuator 808 within a prescribed amount activates a limit switch that indicates that an appropriate basin is in place. As described above, in a preferred embodiment, over-travel of the limit switch indicator would deactivate the limit switch. In this embodiment with the protruding temperature sensor, over-travel would not occur from use of a basin without a thermocouple well 854 as such a basin (not shown) would be prevented by the fixed protruding temperature sensor 804 from depressing the limit switch actuator 808. Over-travel would be rare in this configuration but might indicate that someone has placed something heavy adjacent to the temperature sensor 804 to intentionally or possibly unintentionally depress the limit switch actuator 808.

Examples of suitable materials for the components in FIG. 8 are as follows. The limit switch actuator can be made of Nylon or Delrin as they have low friction and low thermal conductivity. The limit switch guide can be made of polytetrafluoroethylene (PTFE) (commonly known by the registered trademark Teflon). PTFE is resistant to heat and is slippery which works well for the need for the limit switch actuator to move relative to other components. The insulating zone can be made of a silicone which helps seal the system and like PTFE has a high service temperature. A suitable material for this conductive material 816 is an aluminum plate that is 0.032 inches thick. While thicker plates would work, it is a design goal to have minimal thermal mass where possible to make the system responsive.

A number of means can be used to assist the surgical staff in positioning the removable basin so that the thermocouple well is aligned with the thermocouple. For example, providing an alignment line on the removable basin and a corresponding line on the liquid warming device. As the basin is apt to be used with a drape, the alignment line on the liquid warming device would preferably be a light that could be seen through the drape.

Optionally, the placement of the thermocouple well on the basin could be used as a way to ensure that the proper basin from a set of possible basin is being used with a particular warming device. This would be appropriate if it was important to prevent one removable basin with a thermocouple well from being used in the wrong liquid warming device. For example the different device/basin pairs could place the temperature sensing device and corresponding thermocouple well different radial distances from the center of the basin. Another way of preventing the wrong type of removable basin from being used in a particular liquid warming device is to use thermocouple wells of different depths in the different removable basin products. By adjusting the limit switch to require an interaction between the thermocouple and a thermocouple well of a certain depth, the thermocouple well depth can be used to limit the viable choice to a single removable basin product and thus prevent the inadvertent use of wrong removable basin product in the liquid warming device.

A simple way of aligning the thermocouple well with the thermocouple is to place both so that they meet in the center of the removable basin. Such an implementation would need to rely on other attributes in order to prevent an inappropriate basin/device pairing.

An alternative to relying on the thermocouple/thermocouple well interaction to ensure that an appropriate removable basin is inserted in the fluid heating device is to provide the removable basin with an RF ID tag (Radio Frequency Identification tag) and providing a sensor in the liquid warming device. The RF ID tag would be useful whether or not the limit switch tested for an appropriate reaction between the thermocouple and the thermocouple well as it would make it more difficult for a manufacturing entity to sell counterfeit removable basins of inferior quality.

Protection Against Heating Empty Basins

An alternative embodiment would make the limit switch spring loaded so that a basin with an appropriate thermocouple well placed in the proper position would still not enable the limit switch as shown in FIG. 7(B). This alternative embodiment would require the application of more weight than is provided by an empty basin of a known material. In order to enable the limit switch, an additional force, presumably from additional weight from fluid in the basin, would need to be applied. While this additional force could be provided by a gloved thumb of a person in the operating room or a solid object placed in the removable basin, the goal would be to decrease the likelihood that the liquid warming device is applying heat to a removable basin without a substantial amount of fluid. It may be prudent to add an audible or visual alarm to indicate that the liquid warming device is currently not maintaining the sterile fluid at the target temperature as the liquid warming device believes that there is either an improper removable basin or an insufficient amount (weight) of sterile fluid. The use of an alarm will prevent the surgical staff from missing that the fluid heating device is not maintaining the sterile fluid at temperature for use in the surgical procedure.

As the temperature of the heater will normally be selected to be well below the melting temperature of the basin material, it will not normally be necessary to make the limit switch sensitive to the weight or lack of weight of fluid in the basin. But this would not address the situation of a basin that becomes empty or nearly empty as the fluid is used during surgery.

One of skill in the art could impose other forms of protection against heating an empty basin such as requiring a user to confirm that an appropriate sterile container and an adequate level of fluid are present by a response to a question posed by the controls during the power-up sequence for the fluid heating device. It is recognized that asking for confirmation of fluid in the basin at the start of the process does not address the situation of a basin becoming empty during the surgery and left while empty or nearly empty in the fluid warming device.

A co-pending application is for a Heating Element for Liquid Warming Device with U.S. Ser. No. 11/209,430. The warming pad disclosed in that application can be advantageously used with the present application with the modification that the warming pad be provided with an opening that runs through the warming pad so that the control system of the liquid warming device can make contact with the thermocouple well in the bottom of the modified basin. The warming pad described in the above-referenced application provides improved thermal contact to the irregularly shaped basin bottom, a heat distribution layer to reduce the differences in temperature across the heating pad surface, and a low thermal mass to improve responsiveness of the warming pad. The combination of the heating pad as modified for use with the control system of the present invention is considered suitable for use with the various preferred embodiments of the present control system.

As the teachings of the present application could be applied to liquid warming devices using other types of heating systems, the two applications have been filed separately in order to make clear that the details disclosed in one application should not be misinterpreted as limitations of the disclosed invention in the other application.

An alternative heating system would use trace wire resistive heating embedded in silicon to convey heat to a low thermal mass plate (such as described in connection with element 816 below) to convey heat to a relatively flat bottomed basin. The heater would typically place the heater temperature detector 116 and the mechanical thermostat 344 in the center of the heater (below the approximate center of the basin). Typically, the resistive trace heater would not run through this center zone with the two measurement components.

Characteristics of Thermocouple Well and Interaction with Temperature Sensor

One characteristic of the preferred basin thermocouple well 854 discussed above is that the edge 858 of the thermocouple well be adapted to depress the limit switch actuator 808 in order to provide sufficient movement of the limit switch actuator 808. In the event of a limit switch actuator 808 connected to a limit switch sensitive to over-travel, then the shape of the edge 858 of the thermocouple well and the shape of the limit switch actuator 808 need to be coordinated so that the presence of an appropriate basin provide the appropriate depression of the limit switch actuator 808.

One of skill in the art will recognize that the use of a thermocouple well that lacks the edge 858 of the well but instead goes from the portion of the thermocouple well adapted to receive the temperature sensor to the flat bottom of the basin would tend to interact with a limit switch actuator by driving the actuator close to flush with the conductive material 816. Over-travel would be extremely rare if the limit switch was adjusted to close when the top of the actuator is flush. Similarly one could have a ring or other shape around the thermocouple well that projects downward so that the basin projection would depress the limit switch actuator below the level of the conductive material 816. Likewise the interaction between the basin and the limit switch actuator 808 does not have to be an interaction that encircles the temperature sensor 804 as shown in FIG. 8.

Another characteristic of a preferred thermocouple well 854 discussed above is that the thermocouple well be made of the same material as the basin 850. As discussed above, the useful attribute of having the thermocouple well being a good thermal conductor to convey changes in fluid temperature through the thermocouple well to the temperature sensor is deemed less important than isolating the temperature sensor 804 from the heater so that the temperature sensor is not unduly influenced by the temperature of the heater and heat plate rather than the temperature of the fluid. Thus, in this application it is preferably to use a material that is not a good thermal conductor so that heat sensed by temperature sensor 804 is substantially the temperature of the fluid in the basin that surrounds the elevated end of the temperature sensor with minimal impact from thermal energy traveling from the conductive material 816 into the wall of the basin 850 and through the thermocouple well 854 to the tip of the temperature sensor 804.

Another characteristic desirable in a thermocouple well 854 is essentially an interference match between the height of a protruding temperature sensor 804 and the corresponding height of the cavity in the thermocouple well 854 so that a basin thermocouple well 854 appropriately positioned on a temperature sensor 804 will abut against the top of the temperature sensor 804. To the extent that manufacturing tolerances cannot be fully controlled, it is better for the thermocouple well 854 to be slightly deeper and thus have a small gap above the temperature sensor than to be too shallow and cause the basin to fail to make good contact with the conductive material 816 and effectively depress the limit switch actuator 808.

Another characteristic desirable in a thermocouple well 854 is essentially an interference fit between the sides of the temperature sensor 804 and the corresponding portion of the thermocouple well 854. Failure to get a close fit between the walls of the temperature sensor and the thermocouple well may lead to limited contact between the temperature sensor and the thermocouple. While relying nearly exclusively between the contact from the very top of the temperature sensor 804 and the corresponding portion of the thermocouple well 854 would be operative, the small amount of thermal contact relative to the thermal mass of the temperature sensor 804 would tend to decrease the responsiveness of the system to changes in fluid temperature.

One of skill in the art could arrange for an interference fit in a number of ways including ways that expand the thermocouple well to provide the interference fit and ways that compress or otherwise decrease the cross section of the temperature sensor 804. An illustrative example of a preferred embodiment should be sufficient to illustrate the point (discussed in connection with FIG. 9).

Another characteristic desirable in a thermocouple well 854 is the ability to insert the temperature sensor 804 into the thermocouple well without compressing the air present in the empty thermocouple well 854 or forming a vacuum when the basin is lifted off of the temperature sensor 804. Compressing air when placing the basin on the temperature sensor 804 may impede seating the thermocouple well so that it pushes down on the limit switch actuator 808 sufficiently to enable the limit switch 604. Trapping and compressing air may inadvertently add an insulating layer between the top of the temperature sensor 804 and the corresponding section of the thermocouple well 854 and thus decrease the responsiveness of the temperature sensor 804 to changes in the temperature of fluid. A combination of a temperature sensor 804 and a thermocouple well 854 that forms a vacuum when the basin is removed at a normal speed from the warming device would temporarily resist the upward movement of the basin and then let go as the vacuum ceases to operate once the basin has moved a sufficient amount. In an extreme case this could lead to splashing of the sterile fluid out of the basin when a vacuum is formed and extinguished. In most cases it would not lead to splashing but it would be viewed as an undesirable quirk.

One way to prevent both the compression of air in the thermocouple well and the temporary formation of a vacuum during removal of the basin is to add one or more air vents to the thermocouple well. Another way is to select a temperature sensor shape that would not lend itself to compressing air or forming a vacuum. For example, the use of a sloped shape to the temperature sensor such as a frustum, truncated pyramid, hemisphere, or other analogous shape and a corresponding thermocouple well is much less likely to be a problem than a cylindrical temperature sensor inserted into a corresponding cylindrical bore in the thermocouple well.

Figures 9A, 9B, 9C:
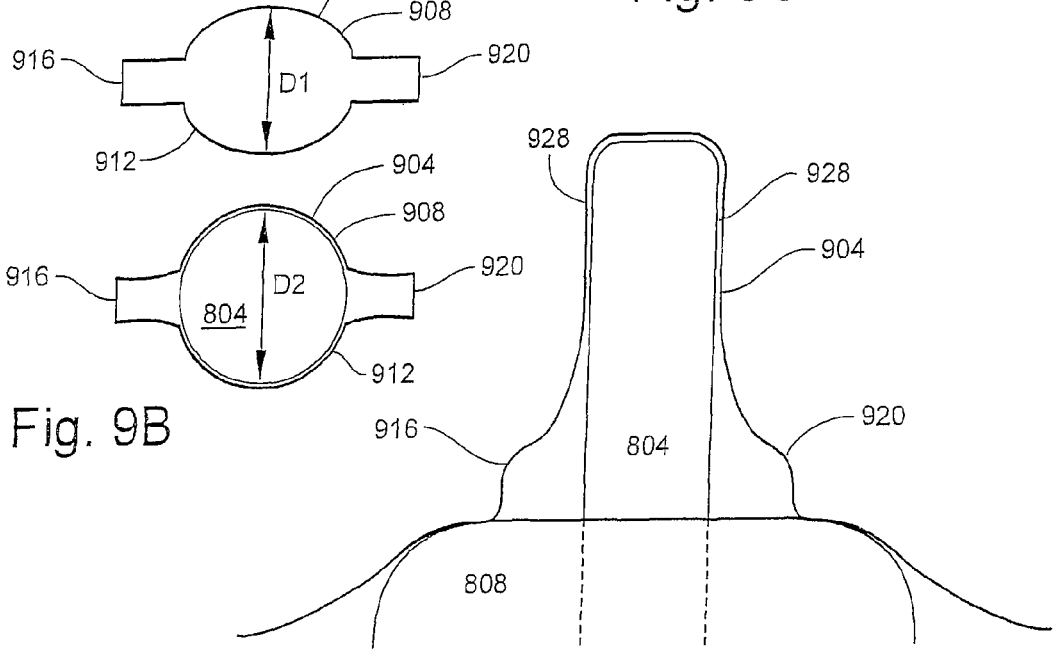
FIGS. 9A, 9B and 9C explain the operation of a thermocouple well using a winged divot to provide an interference fit around a temperature sensor 804.

FIG. 9 shows an example of a suitable thermocouple well in accordance with the characteristics discussed above. This example is meant to illustrate the concepts of a desirable design and is not to scale. FIG. 9A shows a thermocouple well 904 as looking up from the temperature sensor to the bottom of the basin just before the thermocouple well comes into contact with the protruding tip of the temperature sensor. The gap between opposing walls 908 and 912 for the thermocouple well is length D1 for a thermocouple well 904 before insertion of temperature sensor 804. In this example the tip of the temperature sensor is cylindrical with rounded shoulders but having a diameter of more than D1 below the shoulders. Thus, when the tip of the temperature sensor is inserted into thermocouple well 904, the opposing walls 908 and 912 are forced apart to approximately D2, the minimum amount necessary for the temperature sensor 804 to be inserted into the thermocouple well 904. This will lead to a substantially conforming interference fit between the walls of the thermocouple well 904 and the temperature sensor 804 which promotes better tracking of the temperature of the fluid on the other side of the thermocouple well walls.

Well wings 916 and 920 serve two purposes. First, they serve as hinges to allow the flexing of walls 908 and 912 to allow for the interference fit described above. Second the wings help to vent the thermocouple well as the temperature sensor 804 is inserted and removed from the thermocouple well to reduce the tendency to either compress air or to form a vacuum. The shape of the thermocouple well is apt to leave some small amount of gap 928 above the well wings 916 and 920 as the conforming fit will run between the well wings but be less conforming at and above the well wings.

Figure 10A:
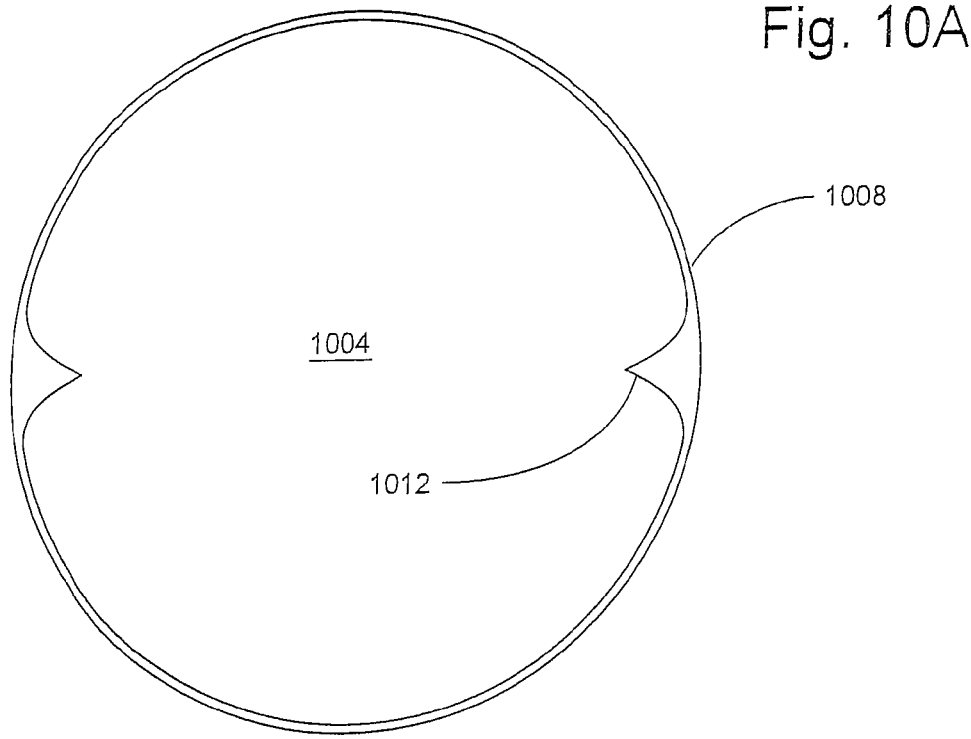
FIGS. 10A and 10B illustrate possible alternative embodiments that provide for venting of air out of and into a thermocouple well (1008 or 1058) as the temperature sensor (1004 or 1054) is inserted and removed.
Figure 10B:
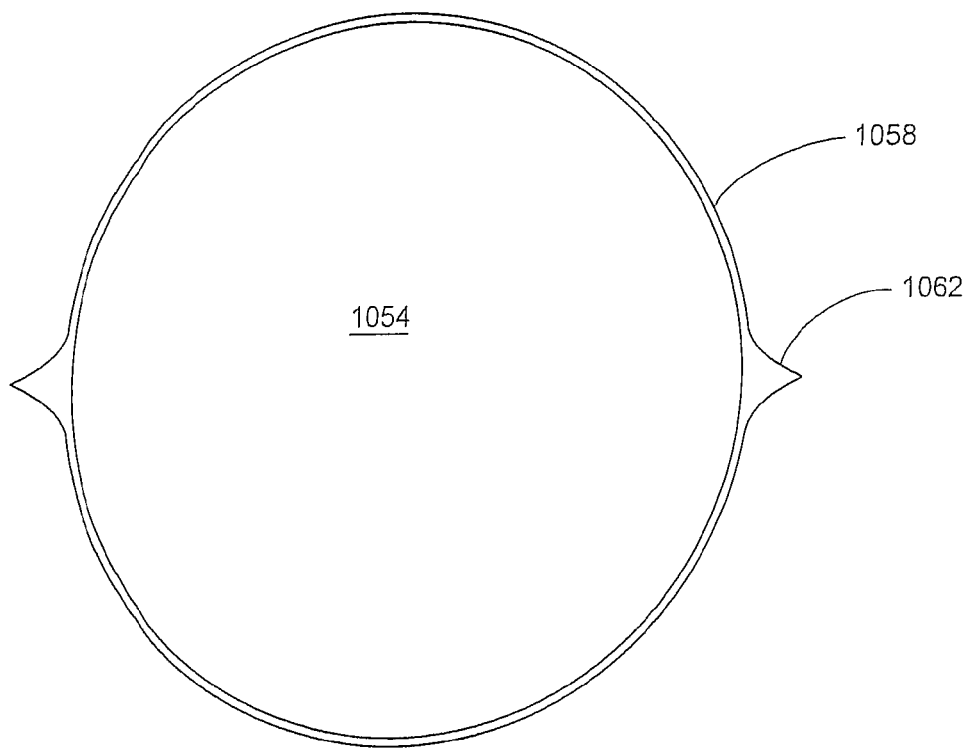

FIG. 10A illustrates that a substantially conforming fit could be obtained by having manufacturing tolerances so that the temperature sensor 1004 has essentially the same shape as the distal tip of the thermocouple well 1008 except for a vent ridge 1012 in the temperature sensor 1004 housing to allow for air to vent out or in during the insertion or removal of the temperature sensor 1004. FIG. 10B is similar except that the vent ridge 1062 is part of the distal tip of the thermocouple well 1058 and the temperature sensor 1054 does not have a vent ridge. (In order to facilitate identifying the various components, the gaps between the temperature sensors and the thermocouple walls are enhanced in FIG. 10).

Another example of a temperature sensor thermocouple well pairing designed to provide a substantially conforming fit is an exterior sheathe connected to the temperature sensor and made of a highly conductive material but is wrapped around the temperature sensor as a helical compression spring that will compress as needed to fit inside the thermocouple well but will expand to make contact with the inside wall of the thermocouple well.

Another example of a pairing designed to provide a substantially conforming fit is to attach the temperature sensor to a thermally conductive sleeve that is an expanding collet-like piece that moves with the limit switch actuator. As the tip of the collet is narrower than the tip of the temperature sensor, when the collet moves downward with the limit switch actuator as the basin moves downward, the temperature sensor tip will be forced into the tip of the collet causing the collet fingers to spread apart and make contact with the thermocouple well wall.

In a variation analogous to that shown in FIG. 10B, the thermocouple well for use with a cylindrical temperature sensor could be slightly elongated in one direction so that the slightly oval thermocouple well would flex to receive the cylindrical temperature sensor and the two end points along the long axis of the oval thermocouple well would serve as vents.

The thermocouple well for use with an essentially cylindrical distal end of a temperature sensor could be a polygon such as a hexagon or octagon that would receive the cylindrical temperature sensor but would have a set of small vents along the corners of the polygon.

These examples just illustrate the range of ways that one of skill in the art can implement this particular teaching of the present invention.

Alternative Control System and Alternative Heaters

The dual set point control system illustrated in FIGS. 3 and 6 is a preferred embodiment of the present invention and uses conventional strip heat technology to provide the heat to the conductive material 816 that is in thermal contact with the basin bottom to heat the fluid 108.

Figure 11:
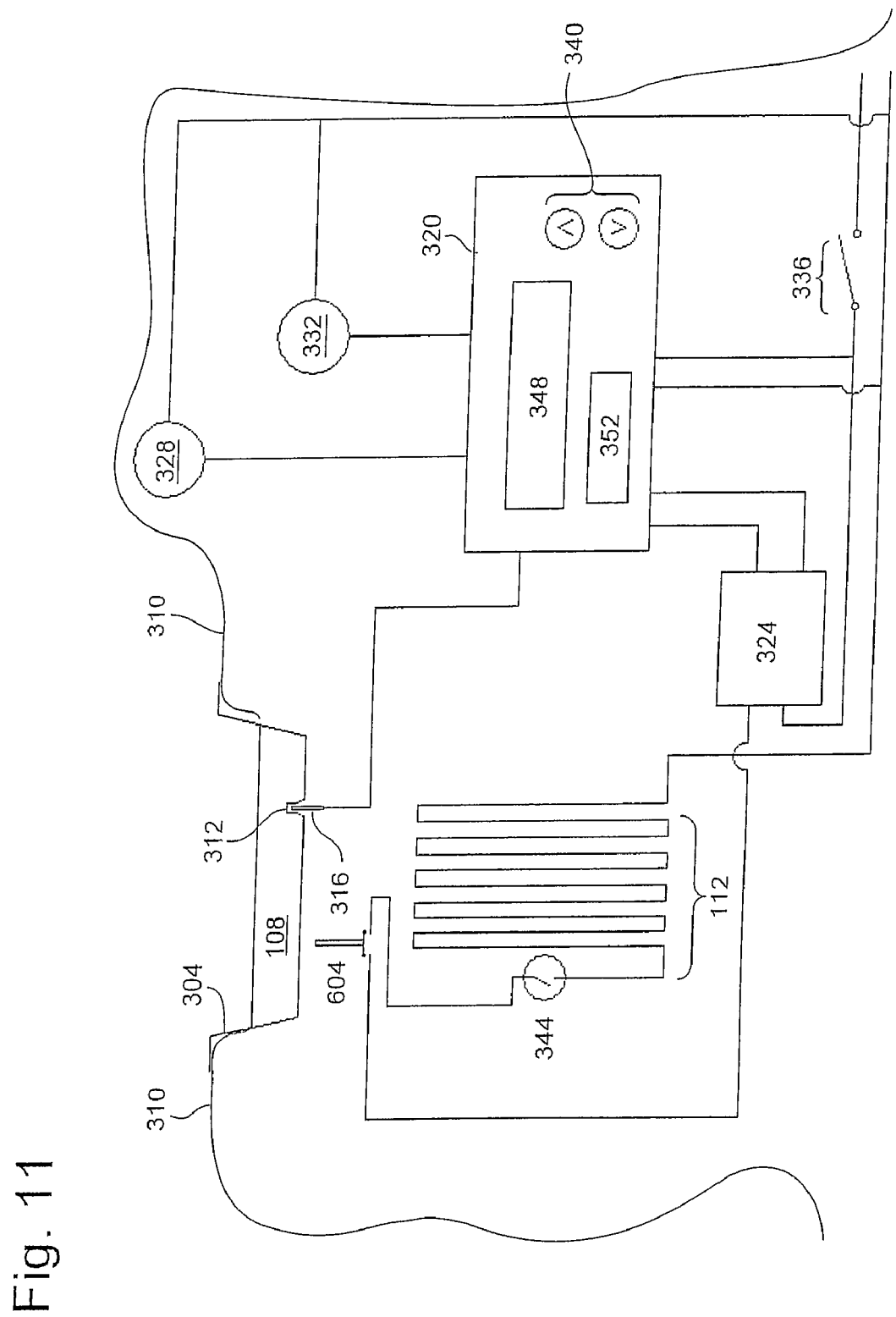
FIG. 11 illustrates a control system using a single set point rather than a dual set point as the embodiment in FIG. 11 does not monitor the temperature of the heater 112.

A control system that delivers energy to a heater based solely on the temperature of the fluid is possible and is part of an alternative embodiment of the present invention. An example of a control system adapted for operation based solely on the temperature of the sterile fluid is shown in FIG. 11. The most striking difference between FIG. 11 and FIG. 6 is that FIG. 11 lacks the heater temperature detector 116 found in FIGS. 6 and 3. Controller 320 attempts to regulate heater 112 through relay 324 to provide suitable thermal input to heat fluid 108 to target temperature 352 as measured by temperature sensor 316 through thermocouple well 312.

In this implementation great care would need to be exercised when heating fluid 108 in a plastic basin 304 to ensure that the local temperature of the heated basin could never exceed the safe operating temperatures of the plastic basin. For instance, if cold water were poured in the basin 304, the controller 320 would detect the large temperature underage and call for the addition of heat by having relay 324 provide current to heater 112. Since there is a lag between heater temperature (now unmeasured) and fluid temperature as sensed by temperature sensor 316, the sensor 316 would continue to detect a temperature underage for a long time and the controller 320 would have no way of determining if it could call for additional heat input without causing the heater 112 to drive the plastic basin bottom above safe limits. In this scenario the heater capacity would need to be reduced so if the heater were on at 100%, the temperature would never exceed the plastic basin safe operation temperature. By monitoring the heater temperature 112 in addition to the fluid temperature as describe in the preferred embodiment, the heater capacity can be larger so that additional heat input can be delivered when needed without compromising the plastic basin.

A control system that does not attempt to measure the temperature of the heater could be used with heaters beyond the resistive heater ("strip heater") discussed above. For example, a system using an infrared heating source to heat the fluid, perhaps from above could be operated using the control system set forth in FIG. 11. Note that the drape 310 would need to be selected and placed relative to the heat source so that the drape is not prone to damage from heat as infra-red heat sources are often extremely hot.

Those of skill in the art will recognize that other heating sources such as microwave, ultrasonic, and induction heating could be used with the control system in FIG. 11 and other teachings of the present invention.

Example of a Preferred Basin

Figure 12:
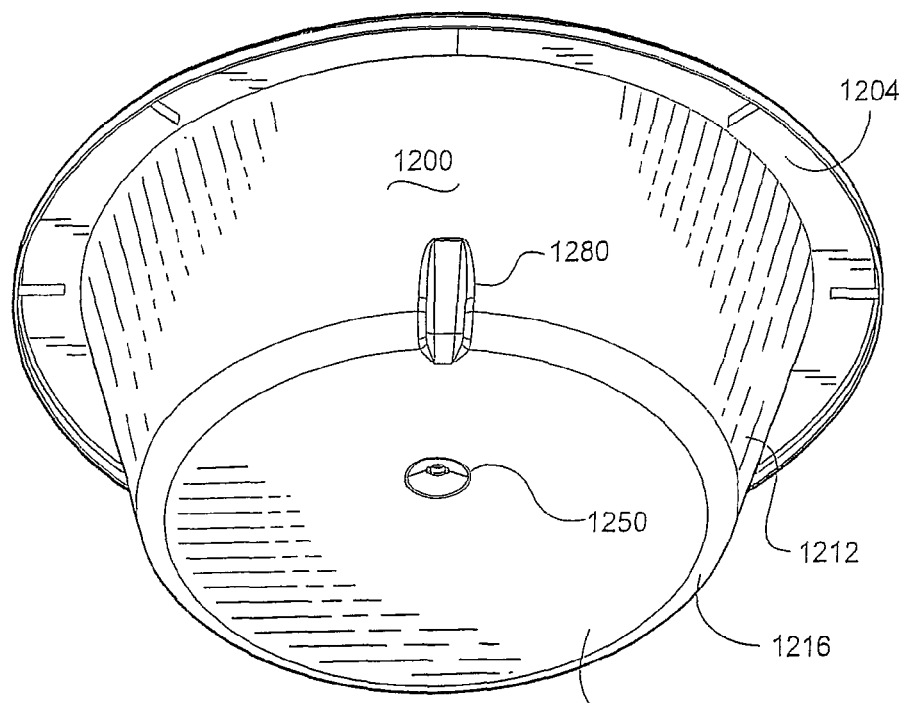
FIGS. 12 through 18 show various views a preferred basin for use with the present invention as this basin has a preferred thermocouple well 1250 and an alignment channel 1280.

FIGS. 12 through 18 illustrate a basin 1200 that can be used in accordance with the present invention. FIG. 12 shows a bottom and side perspective view of basin 1200 with rim 1204, bottom 1208, sidewall 1212, and sloped ring 1216. Thermocouple well 1250 is partially visible. An alignment channel 1280 is present at the intersection of the bottom 1208 and a portion of the sidewall 1212. This alignment channel 1280 fits over a corresponding ridge in the fluid warming device (not shown) to provide an aid in aligning the basin 1200 relative to the fluid warming device so that the temperature sensor can be forced into the interference fit in the thermocouple well 1250. (Note that one of skill in the art can appreciate that an alignment channel would be of value even if the thermocouple well does not require the exertion of force for an interference fit.)

Figure 13:
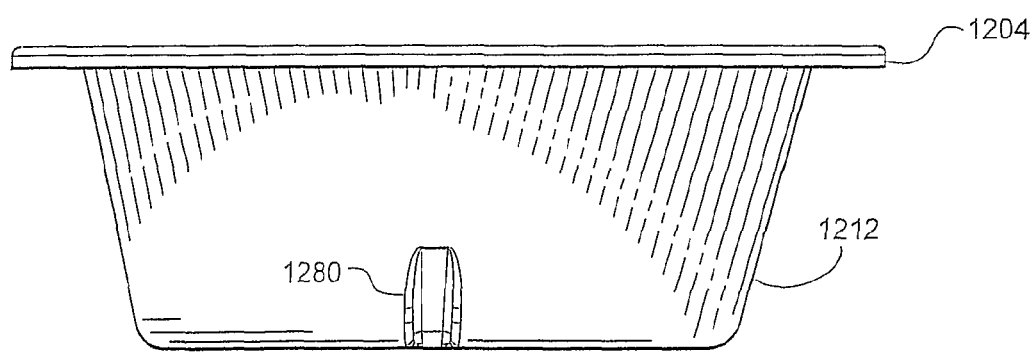

FIG. 13 provides a side plan view of the same basin 1200 with the alignment channel 1280 visible.

Figure 14:
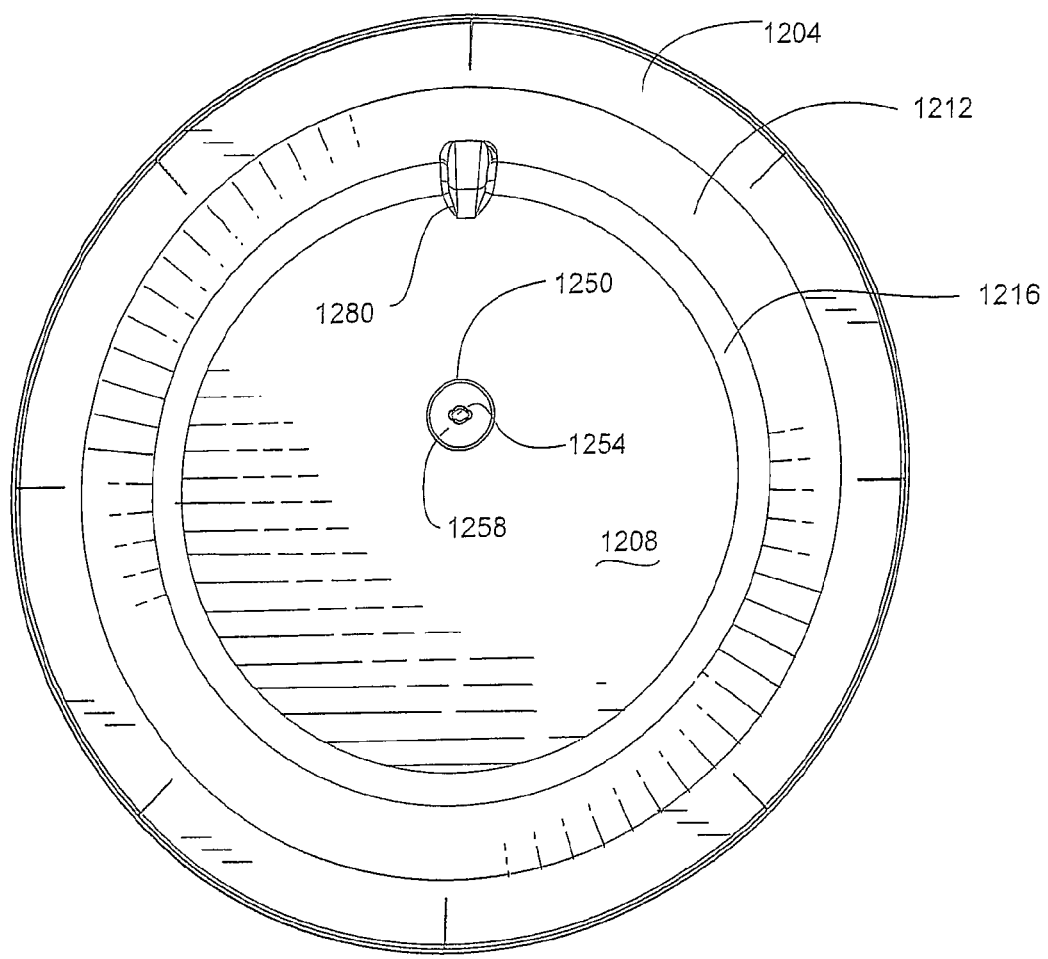

FIG. 14 is a bottom plan view that shows that the center of the thermocouple well 1250 is a winged divot 1254 along the lines discussed in connection with FIG. 9. The winged divot 1254 is surrounded by an indentation ring 1258 that interacts with the limit switch actuator (as shown in FIG. 8 as element 808). When the basin 1200 is forced down upon temperature sensor 804, the indentation ring 1258 is able to move downward in the fluid warming device to depress the limit switch actuator to cause the limit switch (as described in connection with FIG. 7) to close and allow for the provision of energy to the heater.

Figure 15:
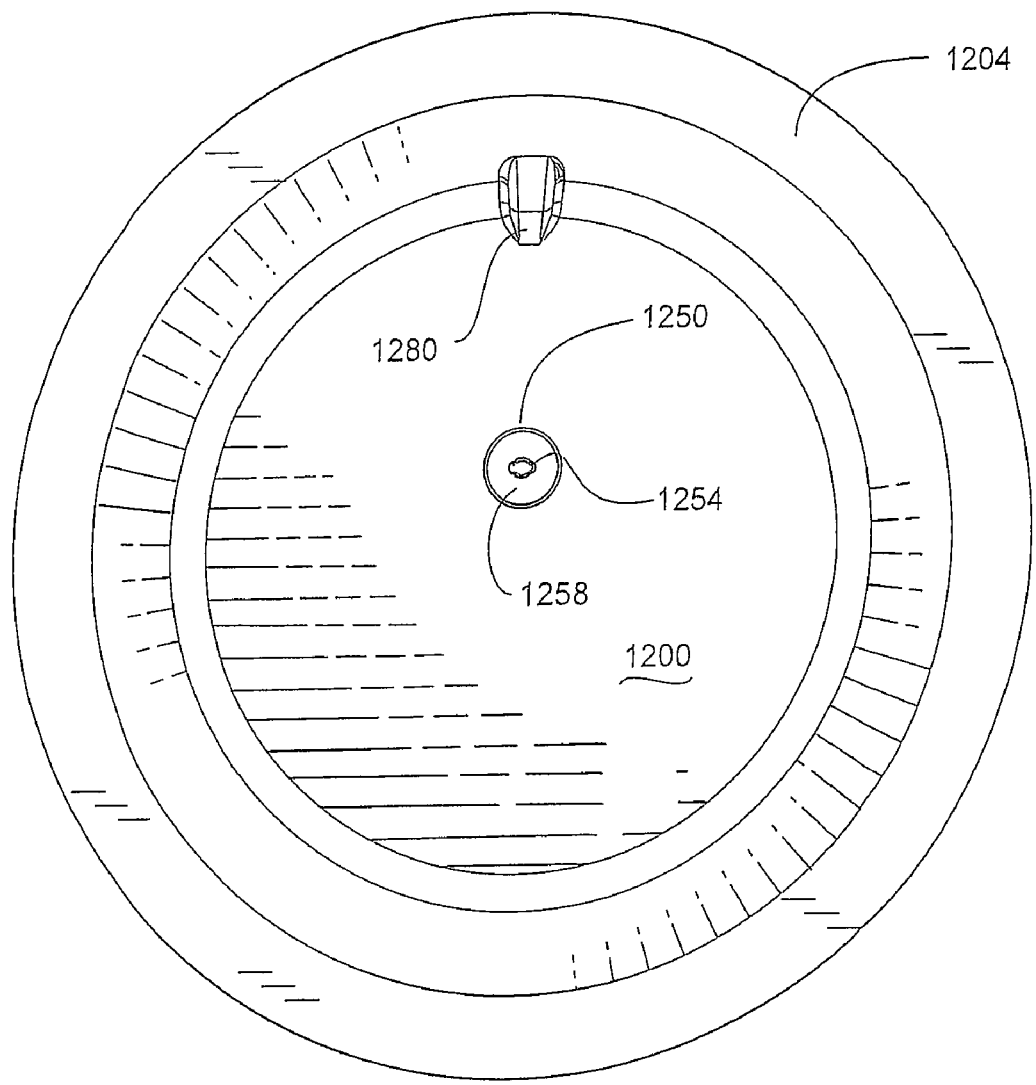

FIG. 15 is a top view of the same basin 1200. Alignment channel 1280 and thermocouple well 1250 extend into the bottom 1208 of the basin 1200 as shown in FIG. 14 but stick out into the fluid holding portion of the basin 1200 as shown in FIG. 15.

Figure 16:
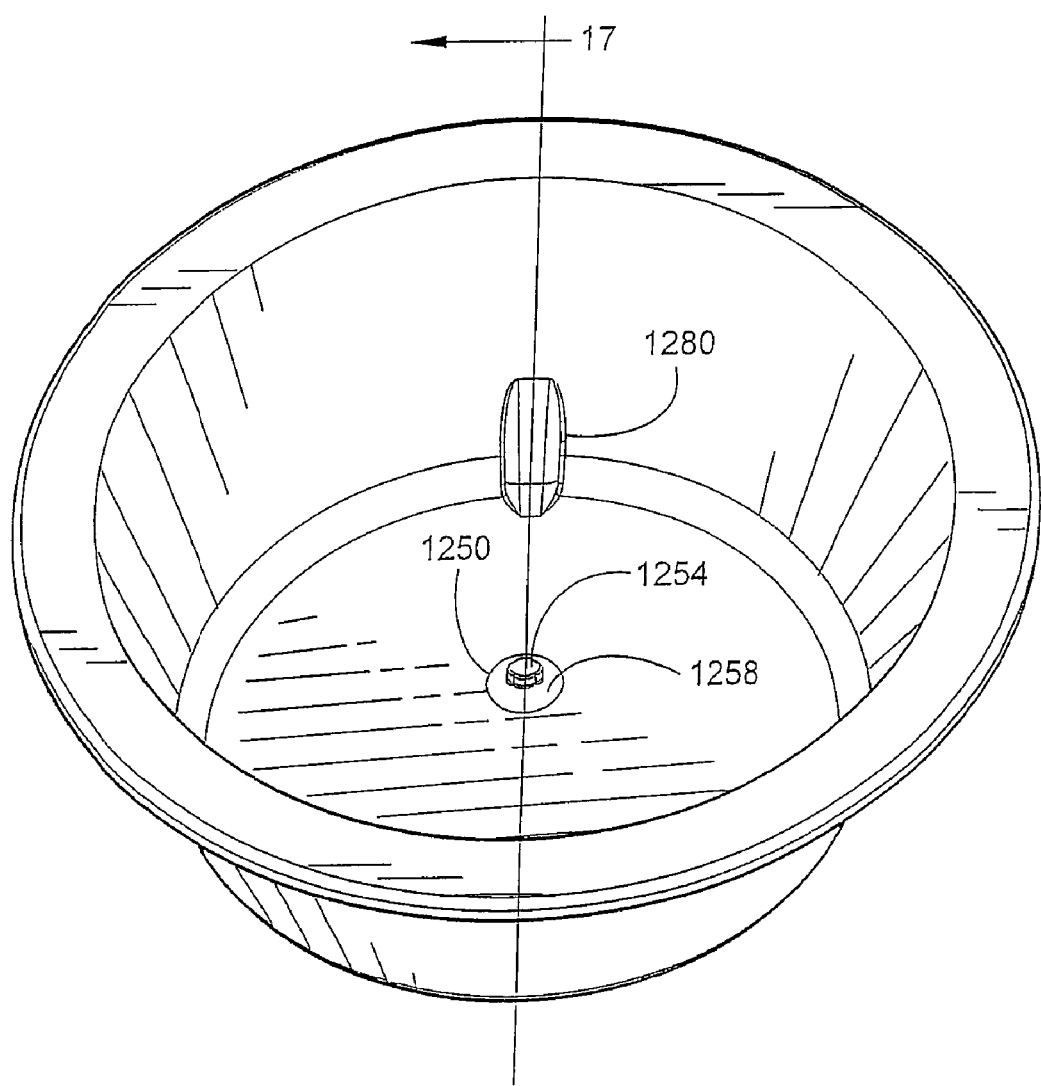
Figure 17:
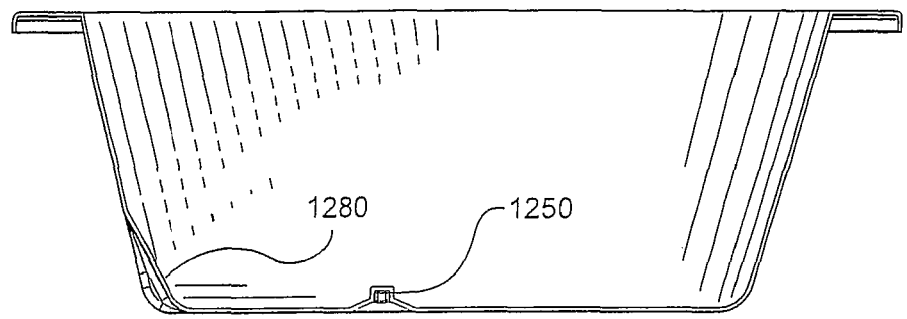
Figure 18:
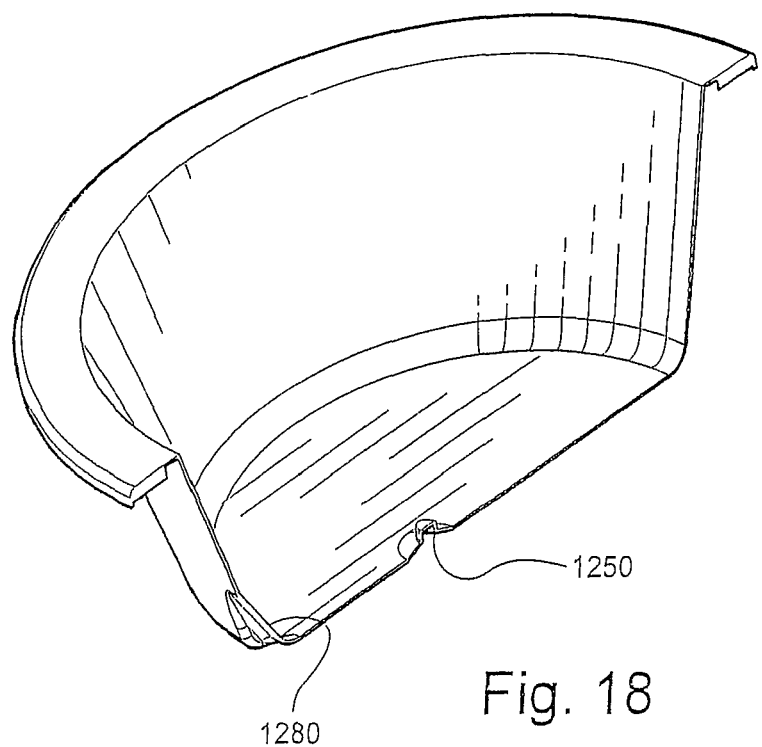

The extension of the thermocouple well 1250 into the basin is easier to see in FIG. 16 which shows a top and side perspective view of the basin 1200. The winged divot 1254 is seen extending above the indention ring 1258. A cross section taken through the alignment channel 1280 and the thermocouple well 1250 is shown in a side view in FIG. 17 and a top perspective view in FIG. 18.

The basin 1200 has the thermocouple well 1250 part way between the sidewall and the center of the basin. One of skill in the art will recognize that placement of the thermocouple well near the side walls of the basin is less likely to lead to obtaining a representative temperature of the fluid in the container as there is the possibility of edge effects impacting the measurement. However, one can appreciate that the function of the thermocouple well 1250 and the alignment channel 1280 could be combined by placing the temperature sensor and the limit switch actuator in the ridge that interacts with the basin alignment channel 1280 and eliminating the thermocouple well 1250 from the basin. While attractive from the standpoint of simplifying the basin, it is currently thought that a free-standing thermocouple well would provide a better indication of current fluid temperature.

More Alternative Embodiments

One of skill in the art will recognize the ability to replace control devices acting as independent components such as limit switch 604 with components that feed data to a logic device that prevents power from going to the heater unless the data is beyond a threshold or in a range. Such replacements are deemed within the scope of the present invention.

The preferred embodiment is to integrate the drape and the basin before inserting the combination into the fluid warming device, and most preferably, to integrate the two components into a single supplied component for use in the surgery before delivery to the operating room. However, it is a viable alternative to use a drape with an opening suitable to allow the basin to interact with the various components of the liquid warming device yet combine with the drape to isolate the top of the liquid warming device from the sterile field. Optionally, the drape could attach to the top of the liquid warming device or to the walls of the cavity in the liquid warming device before the insertion of the basin. As the drape will only be positioned on the liquid warming device for a moment until the basin is placed through the hole in the drape, the drape would not have to be attached to either the basin or the liquid warming device as it could simply be held in place until the basin is inserted.

One of skill in the art will recognize that alternative embodiments set forth above are not universally mutually exclusive and that in some cases alternative embodiments can be created that implement two or more of the variations described above. In a like manner, one of skill in the art will recognize that certain aspects of the present invention can be implemented without implementing all of the teachings illustrated in any of the various disclosed embodiments. Such partial implementations of the teachings of the present invention fall within the claimed subject matter unless the claims are explicit in calling for the presence of additional elements from other teachings.

For example, the preferred location for placement of the temperature sensor is in a thermocouple well protruding out into the fluid to be measured. The present invention has many aspects and one could place a temperature sensor that was in another location such as contacting the bottom or side of the basin (perhaps augmented through use of a spring to ensure solid contact) and still use other claimed aspects of the present invention.

In order to promote clarity in the description, common terminology for components is used. The use of a specific term for a component suitable for carrying out some purpose within the disclosed invention should be construed as including all technical equivalents which operate to achieve the same purpose, whether or not the internal operation of the named component and the alternative component use the same principles. The use of such specificity to provide clarity should not be misconstrued as limiting the scope of the disclosure to the named component unless the limitation is made explicit in the description or the claims that follow.

In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

Those skilled in the art will recognize that the methods and apparatus of the present invention have many applications and that the present invention is not limited to the specific examples given to promote understanding of the present invention. Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalencies. Those unfamiliar with the legal tests for equivalency should consult with a person registered to practice before the United States Patent and Trademark Office.

What is claimed is:

1. A liquid warming device comprising:
a cavity adapted to receive a portion of a removable basin, the removable basin having a bottom, a set of at least one side wall connected to the bottom of the removable basin so that the set of at least one side wall forms a walled perimeter around the bottom of the removable basin to form a container suitable for holding a fluid, and a thermocouple well placed in the bottom of the removable basin and positioned in the cavity;
a heater adapted to provide heat through a thermally conductive path to the fluid placed in the removable basin;
a fluid temperature controller controlling a flow of energy provided to the heater so as to prevent the heater from operating without a positive indication of a presence of an appropriate removable basin;
a fluid temperature sensor used to obtain a temperature from a surface of the removable basin;
wherein the positive indication is received from a limit switch which is implemented with an actuator;
wherein the limit switch is actuated by an insertion of an appropriate removable basin into the cavity;
wherein the removable basin is placed to align the thermocouple well above the fluid temperature sensor and wherein the removable basin pushes down on the actuator which moves downward relative to the fluid temperature sensor and activates the limit switch to a closed position which indicates that an appropriate removable basin is in place in the cavity;
wherein when the thermocouple well is not in its intended position above the fluid temperature sensor, the removable basin does not push down on the actuator and the limit switch remains in an open state;
wherein the limit switch is open:
(a) if there is not an appropriate removable basin in the cavity; or
(b) if an appropriate removable basin is placed in the cavity but the thermocouple well is not aligned above the fluid temperature sensor; and
wherein the liquid warming device provides an indication to users when the limit switch detects an appropriate removable basin but the limit switch is not activated by the actuator and remains in the open state.

2. The liquid warming device of claim 1 wherein the actuator is placed adjacent to a portion of the fixed fluid temperature sensor used to obtain a temperature from a surface of an appropriate removable basin.

3. The liquid warming device of claim 1 wherein the actuator is positioned so as to surround a portion of the fluid temperature sensor so as to insulate the fluid temperature sensor from heat flowing from the heater to the fluid temperature sensor without passing into the fluid in the appropriate removable basin.

4. The liquid warming device of claim 1 wherein the actuator is placed so that interaction between the actuator and the appropriate removable basin is remote from the interaction between the fluid temperature sensor and a portion of the surface of the appropriate removable basin.

5. The liquid warming device of claim 1 wherein the fluid temperature controller prevents the heater from operating without a positive indication from a radio frequency identification sensor that an appropriate radio frequency identification tag is in proximity to the radio frequency identification sensor.

6. The liquid warming device of claim 1 wherein the fluid temperature controller prevents the heater from operating unless the fluid temperature controller has both:
(a) a positive indication from a radio frequency identification sensor that an appropriate radio frequency identification tag is in proximity to the radio frequency identification sensor; and
(b) a positive indication received from a limit switch that is actuated by the insertion of an appropriate removable basin into the cavity.

7. The liquid warming device of claim 1 wherein the positive indication of the presence of an appropriate removable basin is detection of a downward force that may indicate the weight of an appropriate removable basin containing at least a particular minimum volume of a fluid expected to be placed in the removable basin.

8. The liquid warming device of claim 1 wherein the fluid temperature controller controlling the flow of energy provided to the heater so as to prevent the heater from operating without a positive indication of the presence of an appropriate removable basin is adapted to stop preventing the flow of energy to the heater:
while receiving a positive indication of the presence of a downward force that may indicate the weight of an appropriate removable basin with at least a particular minimum volume of a fluid expected to be placed in the removable basin;
until the volume of fluid in the removable basin is decreased sufficiently so that the fluid temperature controller ceases to receive a positive indication of the downward force that may indicate the weight of an appropriate removable basin with at least a particular minimum volume of a fluid expected to be placed in the removable basin.

9. The liquid warming device of claim 1 wherein the lack of a positive indication of the presence of a downward force that may indicate the weight of an appropriate removable basin with at least a particular minimum volume of a fluid expected to be placed in the removable basin activates an alarm to note the fluid temperature controller is preventing the flow of energy to the heater.

10. The liquid warming device of claim 1 wherein the positive indication of the presence of an appropriate removable basin is an affirmation provided by a user through an input device in communication with the liquid warming device that a removable basin and an adequate level of fluid are present.

\* \* \* \* \*